(12) United States Patent
Lawin et al.

(10) Patent No.: US 10,072,241 B2
(45) Date of Patent: Sep. 11, 2018

(54) CONICAL DEVICES FOR THREE-DIMENSIONAL AGGREGATE(S) OF EUKARYOTIC CELLS

(71) Applicant: INNOVATIVE SURFACE TECHNOLOGIES, INC., St. Paul, MN (US)

(72) Inventors: Laurie Lawin, New Brighton, MN (US); Briana Vogen, Falcon Heights, MN (US); Daniel Guire, Maplewood, MN (US); Tahmina Naqvi, Blaine, MN (US); Leandro Forciniti, North Canton, OH (US)

(73) Assignee: INNOVATIVE SURFACE TECHNOLOGIES, INC., St. Paul, MN (US)

( * ) Notice: Subject to any disclaimer, the term of this patent is extended or adjusted under 35 U.S.C. 154(b) by 250 days.

(21) Appl. No.: 14/774,996

(22) PCT Filed: Mar. 12, 2014

(86) PCT No.: PCT/US2014/025050
§ 371 (c)(1),
(2) Date: Sep. 11, 2015

(87) PCT Pub. No.: WO2014/165273
PCT Pub. Date: Oct. 9, 2014

(65) Prior Publication Data
US 2016/0032238 A1    Feb. 4, 2016

Related U.S. Application Data

(60) Provisional application No. 61/779,187, filed on Mar. 13, 2013.

(51) Int. Cl.
*C12N 5/00* (2006.01)
*C12M 1/00* (2006.01)
(Continued)

(52) U.S. Cl.
CPC ........... *C12N 5/0062* (2013.01); *C12M 21/08* (2013.01); *C12M 23/02* (2013.01); *C12M 23/12* (2013.01);
(Continued)

(58) Field of Classification Search
CPC .. C12N 5/0062; C12N 2533/30; C12M 21/08; C12M 23/002; C12M 23/12;
(Continued)

(56) References Cited

U.S. PATENT DOCUMENTS

| 3,931,428 A | 1/1976 | Reick |
| 4,199,142 A | 4/1980 | Reick |

(Continued)

FOREIGN PATENT DOCUMENTS

| GB | 2 438 565 A | 11/2007 |
| WO | WO 04/011938 B1 | 9/2004 |

(Continued)

OTHER PUBLICATIONS

International Search Report for corresponding PCT/US14/25050 (3 pages), dated Aug. 12, 2017.

(Continued)

*Primary Examiner* — Michael L Hobbs
(74) *Attorney, Agent, or Firm* — Weaver Legal and Consulting LLC; Karrie Gemignani Weaver

(57) ABSTRACT

Inventive concepts relate generally to the field of cell culture, and more particularly to formation of three-dimensional aggregate(s) of eukaryotic cells. Cell culture vessels including a conical device having an inner surface being hydrophobic; and a frustum defining an open viewing aperture and a narrow end of the conical device are described. Ceil culture vessel arrays, assemblies and kits are described, as well as methods of making and using the devices.

20 Claims, 19 Drawing Sheets

(51) Int. Cl.
*C12M 1/32* (2006.01)
*C12M 1/12* (2006.01)
*C12M 1/34* (2006.01)
*C12M 3/00* (2006.01)

(52) U.S. Cl.
CPC ............ *C12M 23/22* (2013.01); *C12M 23/58* (2013.01); *C12M 25/04* (2013.01); *C12M 25/06* (2013.01); *C12M 41/46* (2013.01); *C12N 2533/30* (2013.01)

(58) Field of Classification Search
CPC ...... C12M 23/22; C12M 23/58; C12M 25/06; C12M 25/04; C12M 41/46
See application file for complete search history.

(56) References Cited

U.S. PATENT DOCUMENTS

| | | | |
|---|---|---|---|
| 6,156,389 | A | 12/2000 | Brown et al. |
| 6,241,949 | B1 * | 6/2001 | Kane ................ B01L 3/5085 422/553 |
| 6,464,983 | B1 | 10/2002 | Grotendorst |
| 6,683,126 | B2 | 1/2004 | Keller et al. |
| 6,767,587 | B1 | 7/2004 | Brown |
| 6,858,284 | B2 | 2/2005 | Nun et al. |
| 7,201,831 | B2 | 4/2007 | Vincent |
| 7,422,627 | B2 | 9/2008 | Wetzig |
| 7,648,833 | B2 | 1/2010 | Kurosawa et al. |
| 7,883,865 | B2 | 2/2011 | Saito et al. |
| 2003/0153078 | A1 | 8/2003 | Libera et al. |
| 2005/0037047 | A1 | 2/2005 | Song |
| 2005/0118711 | A1 | 6/2005 | Nordheim et al. |
| 2006/0029808 | A1 | 2/2006 | Zhai et al. |
| 2006/0252148 | A1 | 11/2006 | Kurosawa et al. |
| 2008/0019952 | A1 | 1/2008 | Kolossov et al. |
| 2008/0026460 | A1 | 1/2008 | Palecek et al. |
| 2009/0018033 | A1 | 1/2009 | Morgan et al. |
| 2009/0191626 | A1 | 7/2009 | Shogbon et al. |
| 2009/0197333 | A1 | 8/2009 | Saito et al. |
| 2009/0239298 | A1 | 9/2009 | Gerecht et al. |
| 2009/0246871 | A1 | 10/2009 | Kurosawa et al. |
| 2010/0068810 | A1 | 3/2010 | Smith et al. |
| 2010/0197013 | A1 | 8/2010 | Kamp et al. |
| 2010/0203287 | A1 | 8/2010 | Jiang et al. |
| 2010/0204777 | A1 | 8/2010 | Storey et al. |
| 2010/0273259 | A1 | 10/2010 | Saha et al. |
| 2010/0317780 | A1 * | 12/2010 | Cheng .................... C08K 9/06 524/269 |
| 2011/0033928 | A1 | 2/2011 | Smith et al. |
| 2011/0086375 | A1 | 4/2011 | Ungrin et al. |
| 2011/0287470 | A1 | 11/2011 | Stoppini |
| 2012/0149051 | A1 | 6/2012 | Kugelmeier et al. |
| 2013/0029412 | A1 | 1/2013 | Reis et al. |
| 2013/0029422 | A1 * | 1/2013 | Goral .................... C12M 23/12 435/402 |
| 2013/0122580 | A1 * | 5/2013 | Tsukada ................ C12M 23/12 435/289.1 |

FOREIGN PATENT DOCUMENTS

WO     WO 06/137787 A1     12/2006
WO     WO 2011/083768 A1 *     7/2011 ............ C12M 41/06

OTHER PUBLICATIONS

Cameron, C.M., et. al., Improved Development of Human Embryonic Stem Cell-Derived Embryoid Bodies by Stirred Vessel Cultivation, Biotech. and Bioeng. 94(5):938-948 (2006).
Dance, A., Enter the Third Dimension: Cell culture goes 3-D with devices that better mimic in vivo conditions, The Scientist, 26: 8 pages. (2012).
Dang, S., et al., Efficiency of Embryoid Body Formation and Hematopoietic Dev.from Embryonic Stem Cells in Different Culture Systems, Biotech. Bioeng. 78:442-453 (2002).
Hopfl et al., Differentiating embyronic stem cells into embryoid bodies, Methods Mol. Biol. 254:79-98 (2004).
Haycock, J.W. 3D Cell Culture: A Review of Current Approaches and Techniques, Methods in Mol. Bio. 695:1-15 (2011).
Hirschhaeuser, F., et al., Multicellular tumor spheroids: An underestimated tool is catching up again, J. of Biotech. 148:3-15 (2010).
Jungmann, N., et al., Synthesis of Amphiphilic Poly(organosiloxane) Nanospheres with Different Core-Shell Architectures, Macromolecules 35, 6851-6857 (2002).
Konno, T., et al., Formation of Embryoid Bodies by Mouse Embryonic Stem Cells on Plastic Surfaces, J. of Biosci. and Bioeng. 100(1):88-93 (2005).
Kurosawa, H., et al., A Simple Method for Forming Embryoid Body from Mouse Embryonic Stem Cells, J. of Biosci. and Bioeng. 96(4):409-411 (2003).
Lee, W.G. et al. A Hollow Sphere Soft Lithography Approach for Long-Term Hanging Drop Methods, Tissue Engineering: Part C, 16:249-259 (2010).
Magyar, J., et al., Mass Production of Embryoid Bodies in Microbeads, Annals of New York Academy of Sciences 944: 135-143 (2001).
Ng, E., et al., Forced aggregation of defined numbers of human embryonic stem cells into embryoid bodies fosters robust, rep. hematopoietic diff., Blood 106(5)1601-1603 (2005).
Pampaloni, F., et al., The third dimension bridges the gap between cell culture and live tissue, Nat. Rev. Mol. Cell Biol. 8:839-845 (2007).
Valamehr, B., et al., Hydrophobic surfaces for enhanced differentiation of embryonic stem cell-derived embryoid bodies, PNAS 105(38) 14459-14464 (2008).
Wang, X., et al., Scalable Producing Embryoid Bodies by Rotary Cell Culture System and Constructing Engineered Cardiac Tissue . . . , Biotechnol. Prog. 22:811-818 (2006).

* cited by examiner

CONICAL DEVICES FOR THREE-DIMENSIONAL AGGREGATE(S) OF EUKARYOTIC CELLS

CROSS REFERENCE TO RELATED APPLICATIONS

The present application is a U.S. 371 national stage entry of International Application No. PCT/US2014/025050, entitled "CONICAL DEVICES FOR THREE-DIMENSIONAL AGGREGATE(S) OF EUKARYOTIC CELLS", filed Mar. 12, 2014 which claims benefit under 35 U.S.C. § 119(e) to U.S. Patent Application Ser. No. 61/779,187, entitled, "TEXTURED HYDROPHOBIC DEVICES FOR THREE-DIMENSIONAL AGGREGATE (S) OF EUKARYOTIC CELLS," filed Mar. 13, 2014, the contents of which is incorporated herein in its entirety for all purposes.

This invention was made with government support under Grant No. 0848918, awarded by the National Science Foundation. The government has certain rights in the invention.

FIELD

Inventive concepts relate generally to hydrophobic conical devices, with a viewing aperture located at the apex of each device. When employed with or as cell culture container(s) (such as plates), these conical devices are useful for growing and observing three-dimensional aggregate(s) of eukaryotic cells. This disclosure also relates to methods for producing and using these conical devices.

BACKGROUND

In biological and medical research, examining the formation of three-dimensional (3D) aggregate(s) of eukaryotic cells, such as tumor cell aggregate(s) and embryoid bodies (EBs), is important for evaluating various drug screenings, biological compatibility, and cell therapies as well as determining gene/protein expression profiles and engineering cell tissue for various purposes. In recent years, in order to alleviate unnecessary animal suffering, considerable effort has gone into growing eukaryotic cell aggregate(s) to simulate such cell growth in vivo.

Classically, in vitro eukaryotic cells have been cultured as a monolayer on two-dimensional (2D) surfaces made of synthetic materials, such as glass and plastic. However, it is generally accepted that in vitro 3D cell aggregate(s) are physiologically more relevant in comparison to 2D cell monolayer(s), and thus can provide a more accurate precursor model in simulating in vivo animal studies. In the last decade, various studies have demonstrated that in vitro 2D cell monolayers do not accurately represent the in vivo microenvironment, nutrient intake, or biochemical processes including protein production. In addition, the gene/protein expression profiles for a variety of cancer and stem cell lines are also very different in 2D and 3D models. In the past decade, many different in vitro methods of growing 3D cell aggregate(s) have been evaluated to accurately simulate in vivo models used in research studies. However, producing a product that facilitates the formation of 3D cell aggregate(s) has proven to be a difficult design challenge.

Aggregate or spheroid size is an important parameter for screening assays. Single, uniform-sized 3D cell aggregates are desirable for repeatability and accuracy in experiments. The generation of a single, uniform sized spheroid per well of a cell culture device allows screening and testing of biochemical compounds, biological agents and infectious organisms as well as allowing for toxicity evaluations. In the case of embryoid bodies (EBs), spheroid size is linked to cell differentiation potential. In widely used hydrophilic dishes for spheroid culture, agglomeration of spheroids is an area of concern. Large agglomerates can produce their own microenvironment, within which cells produce their own growth factors. This makes it harder to control the culture environment and determine the effects of exogenous factors. Therefore, to identify tumor spheroids or EBs as model systems, it is necessary to form them individually in a uniform and reproducible manner with regulated homogeneity in morphology and differentiation status. Indeed, for screening purposes, uniform sized EBs have been shown to have synchronous differentiation potential.

An in vitro technique widely used to grow eukaryotic cell 3D aggregate(s) is referred to as the Hanging Drop Method. This method has proven useful both for growing cancer cell lines into tumor spheroids and for growing embryonic stem cells into EBs. To practice this method, a cell culture medium (e.g., a sterile water solution containing nutrients), having a known concentration of cells, is added as drops to a flat horizontal surface such as glass or plastic (e.g., the underside of a glass Petri dish cover). Sterile water is then placed in the mating bottom portion (e.g., into the mating bottom part of a glass Petri dish) to maintain humidity within the dish. The dish cover with the suspended drops containing cells in culture medium is gently inverted and is placed atop the mating bottom portion. Due to gravity acting on the cell culture drops suspended from the inverted surface, the cells, being heavier than the medium, settle from the cell suspension in the medium to the bottom of the meniscus of each hanging drop. This unique configuration allows for only the top part of the medium (e.g., the part hanging from the Petri dish lid), which is cell-poor, to be in contact with substrate, and, as a result, the cells form 3D aggregate(s) in the cell medium and do not come in contact with any synthetic surface (e.g., glass or plastic) used in 2D monolayer techniques.

However, there are multiple drawbacks to the Hanging Drop Method. For example, the drops of medium are held on the surface of the Petri dish only by surface tension and adhesion forces, resulting in drop size being limited to a volume of 50 µL or less to resist the gravitational force pulling down on each drop. A further drawback to this method is that the drops are accessible only if the Petri dish lid containing the drops is gently inverted. Thus, it becomes difficult to conveniently change the medium surrounding the cells and to periodically observe the growth of the cell aggregate(s) using a microscope. Furthermore, the agitation caused by inverting the dish can easily cause the drops to run together or fall into the bottom half of the Petri dish. Additionally, if the plate is bumped or rocked even slightly, the hanging drops can easily fall into the media or sterile liquid below them, thus making the recovery of the cells/aggregate(s) contained in the drops highly problematic. On average, only 50-60% of aggregate(s) can be recovered using this method. Moreover, this method is inherently incapable of large-scale production.

In some culture devices, the hanging drop plate consists of a body with two coplanar surfaces having a narrow cylindrical- or hyperboloid-shaped communication conduit connecting the surfaces. The liquid drop is added to a widened portion of the inlet compartment located in the top plate and passes through the conduit to reach a circular relief structure located on the underside of the bottom plate that allows the pendant drop to adhere without spreading on the bottom plate. This design allows for convenient access for easily replenishing the liquid. However, the issue of gravitational instability of the pendant drops used to culture the 3D cell aggregate(s) remains unresolved. Additionally, an inverted microscope cannot be employed to observe the hanging drops.

Another culture system describes a method for producing biological organic material in a substantially spherical drop comprising a culture medium, the drop residing on a substrate in a non-adhered state, and the substrate having a water contact angle of at least 150°. In order to maintain the drop in a fixed state, a specially constructed cell culture plate having periodic protrusions to surround each spherical drop is required. The drops are non-adhered and thus can move between the protrusions; this movement may allow the drops to merge together resulting in the undesirable loss of single drops and spheroids. Furthermore, direct microscopic analysis of the cell aggregate(s) in the drop form is not possible without removing the drop and transferring it to a fresh surface or vessel.

BRIEF SUMMARY

In a first aspect, inventive concepts provide cell culture vessels comprising a conical device having an inner surface being hydrophobic; and a frustum defining an open viewing aperture and a narrow end of the conical device. Also contemplated are cell culture vessel arrays comprising a plurality of cell culture vessels conjoined to form an array of conical devices. In further aspects, inventive concepts provide assemblies comprising a cell culture container having at least one chamber, and a cell culture vessel in registration with the chamber. In some implementations, assemblies can comprise a multi-well cell culture plate comprising a plurality of chambers in the form of wells; and a cell culture vessel array, wherein the plurality of cell culture vessels are in registration with the plurality of wells. In still further implementations, kits are described, as well as methods of making and using vessels, arrays, assemblies and kits that include conical devices in accordance with inventive concepts.

In some implementations, this disclosure relates to a hydrophobic conical device with a viewing aperture (hole) located at the apex of the device, the conical device designed for placement into a chamber of a cell culture container. In some aspects, the conical device is designed for placement into a single well of a multi-well cell culture plate or being employed as the multi-well cell culture plate itself. The conical device is constructed in a manner such that when a drop comprising a suspension of eukaryotic cells in medium is placed into the hydrophobic device above the viewing aperture, the 3D cell aggregate(s) forming over time can be observed by employing a microscope for viewing up through the bottom of the cell culture container and up through the viewing aperture. In some implementations, the hydrophobic conical device comprises a textured hydrophobic conical device.

This disclosure also relates to a strip or sheet comprising two or more conjoined hydrophobic conical devices, with a viewing aperture located at the apex of each device, the sheet designed for congruent placement of the conjoined conical devices into the wells of a multi-well cell culture plate; wherein, when a drop comprising a suspension of eukaryotic cells in medium is placed into each conical device above the viewing aperture, the 3D cell aggregate(s) forming over time can be observed by employing a microscope for viewing up through the bottom of the multi-well cell culture plate and up through the viewing aperture of the device. The configuration of two or more conjoined conical devices, forming a cell culture vessel array, can also provide a convenient format for an end user, whereby the user can detach a desired number of conical devices from the strip or sheet at the time of use and in light of the particular cell culture container selected for the application.

This disclosure also relates to a multi-well cell culture plate of multiple hydrophobic conical devices, with a viewing aperture located at the apex of each device, as the plate itself; wherein, when a drop comprising a suspension of eukaryotic cells in medium is placed into each conical well above the viewing aperture, the 3D cell aggregate(s) forming over time can be observed by employing a microscope for viewing up through the bottom of the plate and up through the viewing aperture of the device. Thus, in these aspects, a cell culture assembly can be provided that comprises a cell culture container and a cell culture vessel formed as a unitary device, e.g., a cell culture plate and a conical device formed as a unitary device. The components of the device can be formed separately and joined together (e.g., using an adhesive or snap configuration), or formed together (for example, by molding or other formative techniques described herein).

Inventive concepts can have many advantages when utilized in combination with a cell culture container having multiple wells (such as 12, 24, 48, 96, etc.). For purposes of illustration, these multi-well embodiments will be discussed at length in the present disclosure. However, it will be readily appreciated that the conical devices of the invention are not limited to multi-well formats, but can be used in connection with a wide variety of cell culture containers. For example, one or more conical devices can be placed inside a cell culture plate or tray that includes only one chamber (for example, a deep culture dish or other suitable plate). The plate or tray can include a chamber of any suitable dimensions, and the desired number of conical devices can be placed in the chamber. For example, one conical device can be placed in a single chamber of a cell culture container, or more than one conical device can be placed in the same chamber of a cell culture container.

In further aspects, it can be useful to utilize the conical devices in cell culture containers that can provide a closed environment (for example, cell culture containers that include a lid or other removable cover). In these aspects, such closed environments can help control the humidity of the cell culture environment and thereby minimize or avoid evaporation of cell culture media within the device. However, it is not critical that the conical devices be used in a closed environment. In some implementations, conical devices can be used as free-standing devices or provided on a support such as a stand, platform or rack (such as a test tube rack) that provides raised edges for supporting the upper surface of the conical device (that is, the surface of the conical device that is at the base of the conical element and opposite the viewing aperture), such that the viewing aperture is suspended (i.e., not touching a surface that may interfere with cell culture within the conical device).

In some embodiments, methods for formation of cell aggregate(s) are provided that comprise steps of: (1) placing an amount of cell suspension into a cell culture vessel comprising a conical device having an inner surface being hydrophobic, and a frustum defining an open viewing aperture and a narrow end of the conical device, wherein the cell suspension comprises eukaryotic cells in medium either with or without serum; and (2) allowing the formation of 3D cell aggregate(s) to occur within the cell suspension. Formation and growth of 3D cell aggregate(s) can be periodically observed over time in each cell suspension by employing a microscope for viewing up through the viewing aperture of the conical device. The cell culture vessel can comprise a cell culture assembly that includes a cell culture container (such as a multi-well plate) and a plurality of cell culture vessels conjoined to form an array of conical devices. An aqueous liquid can be placed in one or more chambers of the culture container to control humidity within the culture container. The combination of cell culture container and drop-containing conical device(s) can be covered with a cell culture container lid providing a light-transparent water evaporation barrier.

This disclosure further relates to an improved method for observing the growth of 3D cell aggregate(s) comprising eukaryotic cells, the method comprising the steps of: (1) providing a cell culture container, (2) providing one or more hydrophobic conical devices, with a viewing aperture located at the apex of each device; (3) placing each conical device within one or more chambers of the cell culture container; (4) providing suspensions comprising eukaryotic cells in medium either with or without serum; (5) placing a drop of cell suspension into the top face of each desired conical device, each drop being sufficiently large to be held stationary within each conical device above each viewing aperture; and (6) allowing the formation of 3D cell aggregate(s) to occur within each drop. Growth of 3D cell aggregate(s) over time can be periodically observed in each drop by employing a microscope for viewing up through the bottom of the multi-well cell culture plate and up through each viewing aperture. The combination of cell culture container and drop-containing conical device(s) can be covered with a cell culture plate lid providing a light-transparent water evaporation barrier. An aqueous liquid can be placed in one or more chambers of the culture container to control humidity within the culture container. The cell culture container can include one or more chambers (e.g., wells) and in some embodiments, the cell culture container comprises a plate that includes 12 or 24 or 48 or 96 or 384 wells.

This disclosure also relates to methods for forming a cell culture vessel comprising a conical device as described herein, the method comprising steps of: (a) providing a plastic; (b) molding the plastic into a conical device and forming a viewing aperture at the apex of the conical device; (c) applying or providing a textured hydrophobic surface to at least the interior surface of the conical device; and (d) optionally, drying and/or curing the applied coating to produce a hydrophobic conical device. The step (c) of applying or providing a textured hydrophobic surface to at least the interior surface of the conical device can comprise applying a polymer containing nanoparticles to at least the interior surface of the conical device. The textured hydrophobic surface can be applied or provided by other techniques as described herein. In use, a drop comprising a suspension of eukaryotic cells in medium is placed into a conical device above the viewing aperture, and 3D cell aggregate(s) forming over time can be observed by employing a microscope for viewing up through the bottom of the multi-well cell culture plate and up through the viewing aperture.

In some implementations, inventive concepts provide methods for forming a cell culture vessel array according comprising steps of: (a) providing a plastic; (b) molding the plastic into a sheet comprising two or more conjoined textured hydrophobic conical devices and forming a viewing aperture at the apex of each device; (c) applying or providing a textured hydrophobic surface to at least the interior surface of each conical device; and (d) optionally, drying and/or curing the applied coating to produce formed strips or sheets comprising two or more conjoined textured hydrophobic conical devices. In use, a drop comprising a suspension of eukaryotic cells in medium is placed into a conical device above the viewing aperture, and 3D cell aggregate(s) forming over time can be observed by employing a microscope for viewing up through the bottom of the multi-well cell culture plate and up through the viewing aperture.

In addition, this disclosure relates to a method for forming a multi-well cell culture plate of multiple textured hydrophobic conical devices, with a viewing aperture located at the apex of each device, as the plate itself, the method comprising the steps of: (1) providing a plastic; (2) molding the plastic into a plate of multiple conical devices and forming a viewing aperture located at the apex of each device: (3) applying or providing a textured hydrophobic surface to at least the interior surface of each conical device; and (4) optionally, drying and/or curing the applied coating to produce a plate of multiple textured hydrophobic conical devices with a viewing aperture located at the apex of each device; wherein, when a drop comprising a suspension of eukaryotic cells in medium is placed into each conical device above the viewing aperture, the 3D cell aggregate(s) forming over time can be observed by employing a microscope for viewing up through the bottom of the multi-well cell culture plate and up through the viewing aperture.

In some implementations, kits are provided that comprise: (a) a conical device having an inner surface being hydrophobic and a frustum defining an open viewing aperture and a narrow end of the conical device; and (b) a cell culture container comprising one or more chambers for cell culture. The cell culture container can comprise a cell culture plate containing one or more wells. In some implementations, kits can comprise: (a) a cell culture vessel array comprising a plurality of cell culture vessels, each cell culture vessel comprising a conical device having an inner surface being hydrophobic and a frustum defining an open viewing aperture and a narrow end of the conical device; and (b) a cell culture container comprising one or more chambers. The cell culture container can comprise a multi-well cell culture plate comprising a plurality of wells. Optionally, kits can further comprise one or more aliquots of a cell culture medium (such as growth medium), a buffer solution, and the like.

This disclosure offers several benefits that can contribute to its ease of use. Unlike the Hanging Drop Method, the cell culture-containing drops are not easily dislodged by, for example, vibration or movement of the cell culture plate. Even if violent vibration (e.g., dropping of the cell culture plate) were to cause the drops located in conical device(s) to fall down through the viewing aperture, the cell aggregate(s) growing in each drop could easily be recovered from the bottom of each well in the well plate that is positioned directly below each device. In addition, replenishment of the medium bathing the 3D cell aggregate(s) can be performed easily by removing some of the used cell medium that surrounds the cell aggregate(s) in small aliquots and replacing it with fresh cell medium. This medium replacement can also be streamlined by employing automated dispensing devices for high throughput applications.

Additional advantages of inventive concepts can include, but are not limited to: (1) the option to make 3D cell aggregate(s) in medium that does not contain serum; (2) the ability to prevent the fusion of drops during testing; (3) the ease of microscopic observation and evaluation of 3D cell aggregate(s); (4) high throughput production capability; (5) the drop size can be up to about 90 to about 150 µL for a device designed for or using a standard 96-well cell culture plate, hence minimizing evaporation issues; (6) medium changes are less frequent and are much easier, (7) direct microscopy can be conveniently used to observe and monitor 3D cell aggregate(s) growth; (8) the ability to generate a single 3D spheroid per well; (9) the ability to offer a well-defined platform that exhibits superior size control of the aggregates; and (10) the ability to perform assays directly in the device and to view results within the device itself.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
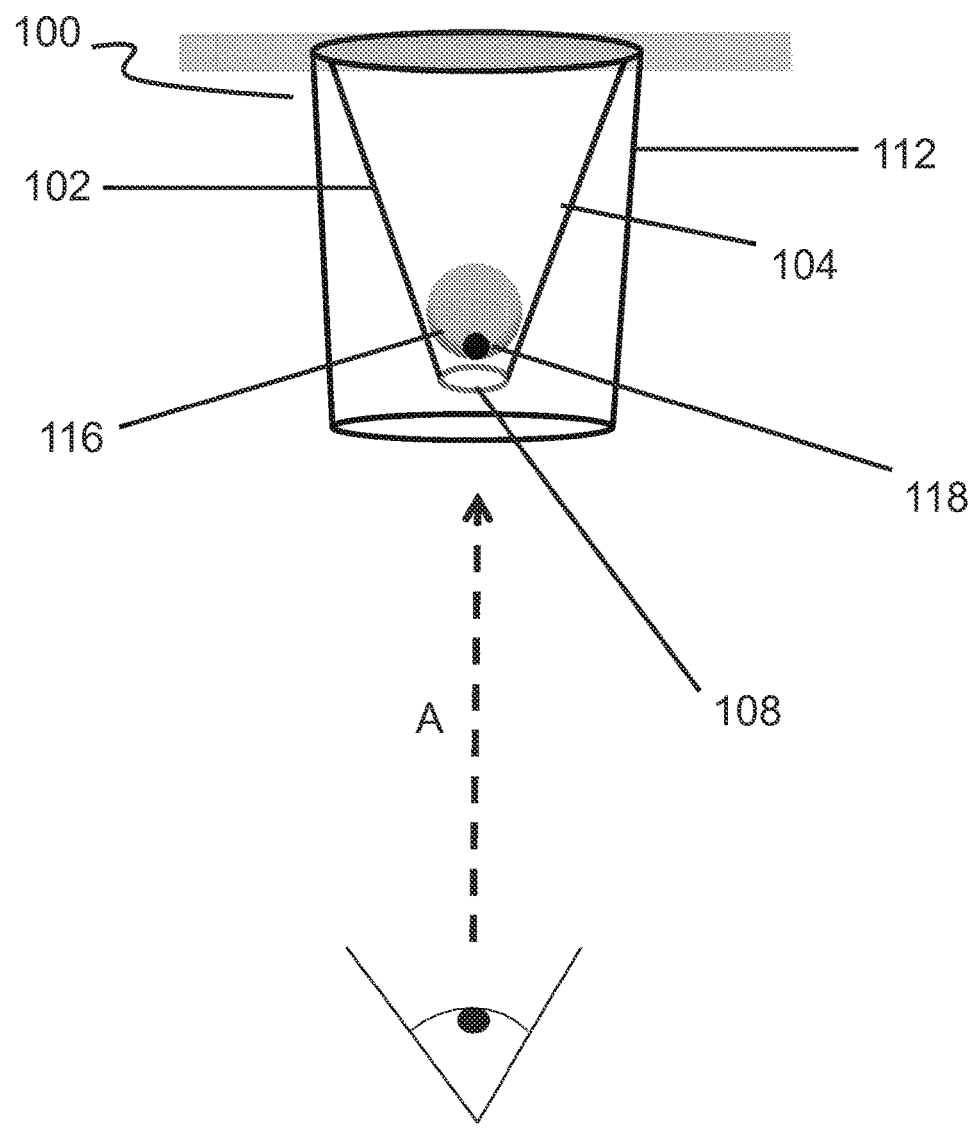
FIG. 1 is a schematic diagram of a single textured hydrophobic conical device placed in a single well of a multi-well cell culture plate depicting a drop of eukaryotic cell suspension in growth medium above the device viewing aperture.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on," "connected to," "coupled with," or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example.

The term "contact angle" is the angle where a liquid interface meets a solid surface. Contact angle was determined herein with a modified Micro Vu 400 Goniometer (Winsor, Calif.), modified with an x, y, z stage and a replacement light. The light was turned on and the sample was placed on the stage to determine contact angle herein. A 10 microliter drop of deionized water was dispensed with an air displacement adjustable micropipette onto the sample. Immediately after the drop was placed on the sample, the drop was brought into focus by moving the stage and a picture of it was taken. The contact angles were determined from the photo using a protractor.

The term "hydrophobic" refers to a surface that produces a contact angle of at least 70 degrees. The term "superhydrophobic" refers to a surface that produces a contact angle of at least 140 degrees.

A purpose of this disclosure is to provide a simple system useful for the growth and observation of eukaryotic 3D cell aggregate(s). To accomplish that goal, inventive concepts utilize hydrophobic conical devices, the conical devices having viewing apertures located at their apexes. The conical devices can be designed for fitting into the chambers of a variety of cell culture containers, such as the wells of commercially available multi-well cell culture plates. The shape of the conical device includes pyramidal shapes with three to an infinite number of sides. The conical devices are designed in such a way as to have their viewing apertures located as closely as possible to the bottom of each well without touching the bottom in order to ensure observation of the culture in the available focal planes of a standard inverted microscope.

The viewing aperture or aperture is formed by truncating a conical element with a truncation plane being parallel to a base of the conical element. In many embodiments these conical devices with a viewing aperture are described as comprising a frustum of a circular cone or pyramid. In preferred embodiments, the conical device has a complex conical structure, meaning that the conical device has at least two different taper angles. In these embodiments the conical device has a larger taper angle near the truncation plane or viewing aperture. Illustrative embodiments of complex conical structures are described herein as "modified" conical structures; additional modifications to the conical structure can be made in accordance with inventive concepts. In some embodiments the first taper angle is in a range from 2 to 15 degrees and the second taper angle is in a range from 3 to 25 degrees. In other embodiments, the first taper angle is in a range from 2 to 15 degrees and the second taper angle is in a range from 15 to 89 degrees. In some embodiments the second taper angle is at least 5 degrees, or 10 degrees, or 20 degrees, or 30 degrees, or 40 degrees greater than the first taper angle.

In use, a drop containing a suspension of eukaryotic cells in medium is placed into each conical device from the top (the base of the conical device). The drop positions itself near the bottom of the cone apex above the viewing aperture. The growth of 3D cell aggregate(s) in the drop can then easily be observed by employing a conventional inverted microscope.

Inventive aspects will now be described with reference to FIG. 1. The schematic in FIG. 1 illustrates the basic concept of this disclosure, showing a single conical device containing a drop of cell medium placed in a single well of a multi-well cell culture plate above the viewing aperture of the conical device. This disclosure is not limited to a device for a multi-well cell culture plate and includes a plate with multiple hydrophobic textured conical devices already designed as part of the plate itself. In addition, a preformed plate with conical or pyramidal wells could be modified by placing an aperture at the apex of each well and modifying the surface of the well to be hydrophobic and textured.

FIG. 1 is a schematic diagram of a cell culture vessel 100 including a conical device 102, the conical device 102 having an inner surface 104. As illustrated, a single conical device 102 is placed in a single well 112 of a multi-well cell culture plate. In use, a drop of eukaryotic cell suspension in growth medium 116 is provided into the conical device 102. The cell suspension positions itself above the device viewing aperture 108. Over time, cell aggregate(s) 118 can form within the cell culture vessel 100, and such cell aggregate(s) 118 can be visualized through the viewing aperture 108. The line of sight through the viewing aperture 108 is indicated at A within the figure.

Although conical devices of this disclosure can be placed individually into each well of a multi-well cell culture plate, it is generally more convenient to simultaneously place a strip or sheet or layer of multiple conjoined conical devices into the wells. Molded polymer sheets containing two or more conjoined textured hydrophobic conical devices of this disclosure can be constructed of appropriate size to fit congruently into conventionally used multi-well cell culture plates, for example, strips or sheets containing 12, 24, 48, 96, or 384 conjoined textured hydrophobic conical devices that fit into a 12-, 24-, 48-, 96-, or 384-well cell culture plate, respectively. A general schematic illustrating the congruent fitting of a molded sheet of conjoined conical devices of this disclosure into a cylindrical multi-well cell culture plate is shown in FIG. 2.

Figure 2:
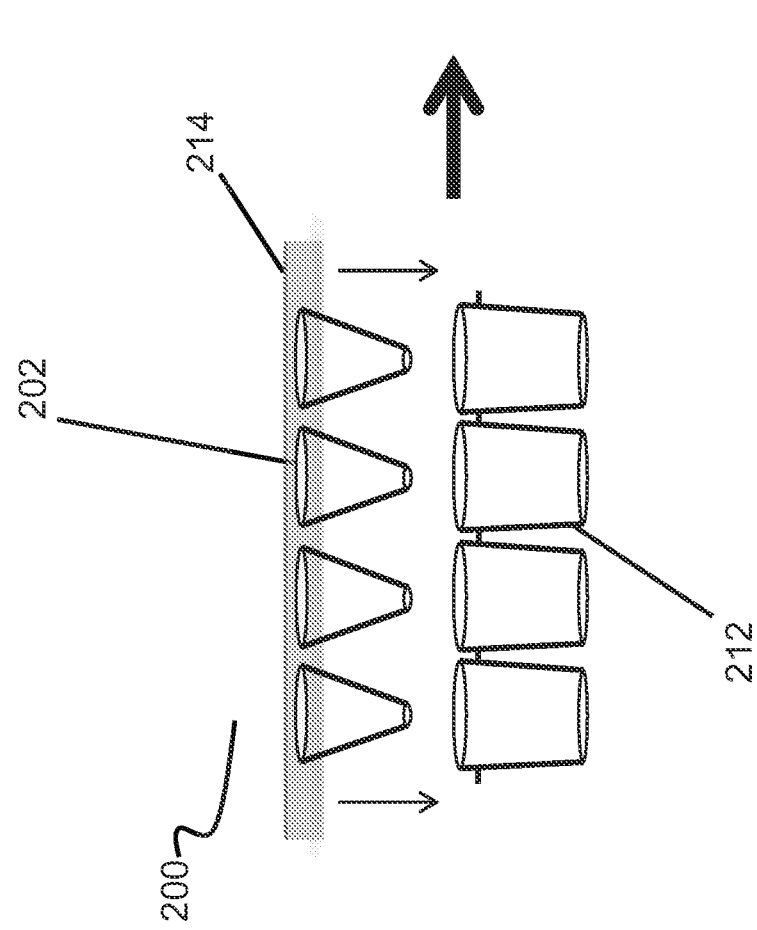
FIG. 2 is a schematic diagram of a molded sheet containing conjoined conical devices fitting into a standard 96-well plate for 3D cell culture.

As illustrated in FIG. 2, a cell culture vessel 200 includes conjoined conical devices 202 of a sheet 214, thereby forming a cell culture vessel array. In use, the conjoined conical devices 202 can be inserted into wells 212 of a selected multi-well plate, thus forming a cell culture assembly 220.

Any method that produces conical devices of the desired dimensions can be used, including but not limited to thermoforming, vacuum molding, injection molding, resin injection molding, reaction injection molding, blow molding and rotational molding, selective laser sintering, selective heat sintering, stereolithograpy, fused deposition modeling, and digital light processing.

The conical device can be fabricated out of any polymer that can provide a surface amenable for texturing or for coating with a textured hydrophobic coating. Useful polymers (or polymer blends) for fabricating the device can be either hydrophobic (i.e., exhibiting a stationary water contact angle of greater than or equal to about 70 degrees) or hydrophilic (i.e., exhibiting a stationary water contact angle of less than about 70 degrees). Preferably, the polymer (or polymer blends) exhibits a stationary water contact angle of greater than about 60 degrees. Examples of useful classes of polymers are well known and can include, for example, oligomers, homopolymers, copolymers and graft copolymers, resulting from addition, reaction, and condensation polymerizations of monomers. Examples of suitable addition monomers include, but are not limited to, acrylics, and olefins and styrenes such as those polymerized from C1 to C12 acrylates and methacrylates, C1 to C12 fluorinated acrylates and methacrylates, hydroxyethyl methacrylate, hydroxyethyl acrylate, acrylic acid, methacrylic acid, glyceryl acrylate, glyceryl methacrylate, methacrylamides, and acrylamides; and vinyls such as ethylene, propylene, butylene, isoprene, methylpentene, styrene, vinyl chloride, vinyl acetate, alkyl vinyl ethers, acrylonitrile, tetrafluoroethylene, vinylidine dichloride and vinylidene difluoride. Examples of suitable polymers classes from reaction polymerizations include, but are not limited to, polyurethanes, polyimides, epoxies, polyetherketone, polysulfones and phenolics. Examples of condensation polymers include, but are not limited to, polyamides such as polycaprolactam, poly(lauryl lactam), polyhexamethylene adipamide, and polyhexamethylene dodecanediamide, as well as polyesters such as polycaprolactone, polylactide, polyglycolide and poly(ethylene terephthalate), as well as cellulose, and polycarbonates. An example of a useful graft polymer is high-impact polystyrene. Other suitable polymers include silicone elastomers, polydimethylsiloxanes and polyoxymethylene.

In some embodiments, conical devices can be fabricated from suitable ceramics, such as, for example, silicon nitride, silicon carbide, zirconia, alumina, glass, silica, sapphire, and the like. The device could also be fabricated from paper or polymer meshes, for example, polypropylene, nylon, polyethylene terephthalate, and polystyrene, each mesh with a pore size ranging from 0.4-250 µm.

In some implementations, conical devices can be fabricated from a composite material that comprises one or more hydrophobic polymers and a texturizing agent dispersed within the polymer. Suitable polymers include those polymers described herein as useful for fabricating the conical device. Illustrative texturizing agents comprise particles. Suitable particles include those described herein for use in textured hydrophobic coatings, among others.

Thus, in some implementations, there is provided a cell culture vessel comprising: a conical device comprising a composite material of one or more hydrophobic polymers and a texturizing agent; and a frustum defining an open viewing aperture and a narrow end of the conical device. The composite material can comprise one or more hydrophobic polymers selected from those described herein, and a texturizing agent selected from any of the particles described herein. Optionally, the particles can be surface treated. Optionally, the conical device can be opaque.

Preferably the device is fabricated from a hydrophobic polymer selected from the group consisting of high-impact polystyrene, acrylonitrile-butadiene-styrene copolymer, polystyrene, polymethylmethacrylate, acrylic, polypropylene, polymethylpentene, and polyvinyl chloride.

Thicknesses of strips or sheets or layers used for molding comprising two or more conjoined conical devices can be in the range of 0.13 mm thick to 0.76 mm thick. For example, 0.5-mm thick high-impact polystyrene sheets can conveniently be thermoformed using standard vacuum molding techniques to produce any desired size and shape of conical device desired to fit congruently into the particular multi-well cell culture plate of interest.

The rim around each viewing aperture, located at the apex of each conical device, should be as smooth as possible. Suitable viewing apertures can be formed by using, for example, an end mill or punch, or formed during the molding process, for example, injection molding. The diameter of each viewing aperture should be sufficiently large to allow clear observation of the 3D cell aggregate(s) growing in each drop of medium but also should be sufficiently small to contain the drop within the apex of the conical device for at least several days of cell aggregate growth. The viewing apertures can be covered with a transparent material. In many embodiments the diameter of each viewing aperture is in a range of about 0.5 to about 2 mm or about 0.75 to about 1.5 mm or about 0.75 to about 1.2 mm.

In accordance with inventive aspects, the inner surface of conical devices provide features that enable formation of 3D cell aggregate(s). In some aspects, the surfaces can be described as textured, meaning that the surface possesses a surface roughness (i.e., the surface is not smooth). The textured feature can be provided by any of the techniques described herein. In some aspects, the surfaces can be described as hydrophobic or even superhydrophobic. In some aspects, surfaces can be described as textured hydrophobic.

In accordance with inventive aspects, a textured hydrophobic surface maximizes the stationary contact angle between the cell medium drop and the interior surface of the conical device. The high stationary contact angle imparted by the hydrophobic textured surface ensures that each drop attains a nearly spherical configuration within the conical device, which minimizes the contact between each growing cell aggregate(s) with the inside surface of the conical device and thus minimizes the undesirable pinning or adherence of cells to the device surface. To be considered a textured hydrophobic surface, the surface exhibits a stationary water contact angle of at least 90 degrees as measured with a drop of distilled water, using a standard stationary contact angle measuring device such as a goniometer, described above. In many embodiments, the textured hydrophobic surface exhibits a stationary water contact angle of at least 110 degrees, or at least 120 degrees, or at least 130 degrees, or at least 140 degrees.

The textured hydrophobic surfaces of this disclosure can be produced by applying a textured hydrophobic coating to the conical device(s). This textured hydrophobic coating can consist of a mixture of one or more hydrophobic polymers having particles consisting of nanoparticles and/or microparticles dispersed within the polymer. Nanoparticles are generally understood to encompass ultrafine particles with lengths in two or three dimensions greater than about 1 nm and smaller than about 100 nm. The length scale may be a hydrodynamic diameter or a geometric length appropriate to the intended use of the nanoparticle (see ASTM E2456-06 and ISO/TS 27687). Microparticles are generally understood to encompass particles with dimensions in the range of about 0.1 μm to about 100 μm in size (IUPAC). The polymer(s) of the coating contribute to surface hydrophobicity and additionally entrap the nano- and/or microparticles within the polymer(s) to impart the desired micro- and nano-texturing to the coating on the surface of each conical device.

In many embodiments, coatings are conveniently applied onto the conical devices and sheets of two or more conjoined conical devices as a solution or dispersion in an application solvent that will not adversely impact the polymer used to construct the conical devices. For example, suitable solvents compatible with the polystyrene conical device construction include volatile alkanes (e.g., n-hexane) and polar solvents (e.g., acetonitrile). Coatings described in this document can be applied by placing each conical device in a scintillation vial containing a solution or dispersion of the desired coating, gently inverting the immersed conical device repeatedly for about 30 seconds, removing the conical device, then optionally blowing the device dry with canned air and allowing the wet coating on the conical device to dry and/or cure for at least 2 hours under ambient conditions. Other useful coating application methods include dipping, spraying, brushing, dabbing, and electrostatic deposition.

Alternatively, the conical device can be textured using other means including but not limited to mechanical means (e.g., grinding, sanding, brushing, blasting with airborne particulates, polishing with particle slurries); or chemical means (e.g, surface modification using chemical baths, plasma, ion beam, laser, electrostatic deposition or chemical vapor deposition); and/or other means (e.g., imprint lithography or generated during device formation).

Useful polymers for the textured hydrophobic coatings of this disclosure should be hydrophobic (i.e., exhibiting a stationary water contact angle of greater than about 70 degrees). Preferably, the polymer (or polymer blends) exhibits a stationary water contact angle of greater than about 80 degrees. Examples of useful classes of polymers are well known and can include, for example, oligomers, homopolymers, copolymers and graft copolymers, resulting from addition, reaction, and condensation polymerizations of monomers. Examples of suitable addition monomers include, but are not limited to, acrylics, and olefins and styrenes such as those polymerized from C1 to C18 acrylates and methacrylates, C1 to C18 fluorinated acrylates and methacrylates, hydroxyethyl methacrylate, hydroxyethyl acrylate, acrylic acid, methacrylic acid, glyceryl acrylate, glyceryl methacrylate, methacrylamides, and acrylamides; and vinyls such as ethylene, propylene, butylene, isoprene, methylpentene, styrene, vinyl chloride, vinyl acetate, alkyl vinyl ethers, acrylonitrile, tetrafluoroethylene, vinylidine dichloride and vinylidene difluoride. Examples of suitable polymers classes from reaction polymerizations include, but are not limited to, polyurethanes, polyimides, epoxies, polyetherketone, polysulfones and phenolics.

Examples of condensation polymers include, but are not limited to, polyamides such as polycaprolactam, poly(lauryl lactam), polyhexamethylene adipamide, and polyhexamethylene dodecanediamide, as well as polyesters such as polycaprolactone, polylactide, polyglycolide and poly(ethylene terephthalate), as well as cellulose, and polycarbonates. An example of a useful graft polymer is high-impact polystyrene. Other suitable polymers include silicone elastomers, polydimethylsiloxanes, and polymers generated from sol-gel reactions.

The polymers in the textured hydrophobic coating can be optionally crosslinked by addition of reagents and/or energy that can cause the polymer to become crosslinked. Suitable reagents include but are not limited to peroxides, oxygen, benzoins, phenones, benziketals, phosphine oxides, phosphonates, azo compounds, azide compounds, triazine compounds, xanthones, thioxanthones, coumarins, quinones, oximinoketones, thiobenzoic S-esters, biimidazaoles, redox reagents, metal catalysts, and derivatives or mixtures thereof. Suitable energy includes but is not limited to heat and radiation such as gamma, electron beam, and visible and UV light. Additionally, the polymers could be optionally functionalized with reactive groups that can cause the polymer to become crosslinked. Suitable reactive groups include but are not limited to unsaturated carbon-carbon bonds, azides, anhydrides, diene and dienophiles, carboxylic acids, carbodiimides, aziradines, amines, acrylamides, ketones, epoxides, peroxides, azalactones, oxazolines, alcohols, and benzophenones.

Preferably the hydrophobic polymer in the textured hydrophobic coating for a polystyrene device is selected from the group consisting of polybutadiene, polyisobutylene, polystyrene-block-poly(ethylene-ran-butylene)-block polystyrene or an acrylic polymer containing both alkyl and fluorinated hydrocarbons.

In accordance with inventive concepts, the particles in the coating are hydrophobic. The polymer matrix entraps the particles on the surface to give the desired micro- and nano-texture. The polymer matrix also provides the surface hydrophobicity. Particles can be pretreated with a silane or a thiol to help increase hydrophobicity of the ultimate composition. Silanation of surfaces is known in the art. Generally, any hydrophobic silane that can react with a surface can be used to treat the particles described herein. In some aspects, particles can include virtually any type of particle that has a particle size between about 1 nm and up to 25 μm, preferably 100-500 nm. The particle can be porous or non-porous. Generally, the particle has an oxide layer but in particular the oxide layer has been treated with a silane reagent to provide hydrophobicity. In many embodiments the particles are present in the hydrophobic coating in an amount of at least about 50% wt.

Suitable materials useful for forming particles include, but are not limited to, silicon dioxides (silica), aluminum oxides (alumina), titanium oxide, zirconium oxide, gold, silver, nickel, iron oxide, and alloys as well as polystyrene, (meth)acrylates, PTFE, polyolefins, polycarbonates, polysiloxanes, silicones, polyesters, polyamides, polyurethanes, polymers made from ethylenically unsaturated monomers, polyanhydrides, polycaprolactone (PCL) and polylactide-glycolide (PLGA). Useful particles may also be in the form of nanofibers, nanotubes, or nanowires and combinations thereof. Preferably the particles are composed of silica. Any type of silica particle can be used in the compositions of the disclosure. The silica can be porous or non-porous and in particular can be treated with a silane to help improve hydrophobicity.

Silanation of surfaces is known in the art. Generally, any hydrophobic silane that can react with a surface can be used to treat the particles described herein. Not to be limited by the following, it is possible to treat uncoated particles using a solution phase reaction. A long chain alkylsilane (e.g., octadecyltrichlorosilane, decyltrichlorosilane) can be used. The alkyl chain length can be varied from about 1 to 20, though a chain length of 18 is very common. Additionally there are useful aryl silanes (e.g., tolyldimethylchlorosilane, phenyltrichlorosilane) and fluoroalkylsilanes (e.g., heptadecafluorodecyltrichlorosilane) having the same hydrocarbon chain length range as straight alkyl chains, with complete or almost complete fluorination.

The silanes can react with the particle surface through reactive groups, such as chloro groups (mono-, di-, and tri-chloro) or through alkoxy groups (e.g., mono-methoxy, di-methoxy, tri-methoxy, or ethoxy versions). Useful silanes can have one, two, or three chains, though it is more common to have one chain, and can have one or two methyl groups. Such silanes are sold commercially by Gelest Inc. (Morrisville, Pa.; www.gelest.com). Application procedures are found in the Gelest catalog, the contents of which are incorporated herein by reference.

A wide variety of cell types and cell lines can be employed for the formation, growth, maturation, and observation of cell aggregate(s) using the conical devices of this disclosure. For example, 3D stem cell aggregate(s) for adult, embryonic, and induced pluripotent stem cells of human, mouse and rat origins can be formed for directed differentiation and screening studies. 3D cell aggregate(s) from liver and kidney cell lines can be tested for toxicity screening. Several tumor cell line aggregate(s) such as cervical cancer (HeLa), colon cancer (RKO, HT29), prostate cancer (ALVA-31 and PPC-1, PC-3), breast cancer (MCF7, T47D), ovarian cancer (A2780) can be tested for the effect of small molecule and drug screens. In addition, the conical devices can also be used to support the formation of spheroids from widely used and well-characterized cell lines such as CHO (Chinese Hamster Ovary cells), HEK (Human Embryonic Kidney cells), HuVec (Human Vascular endothelial cells), and BAEC (Bovine aortic endothelial cells).

It will be readily appreciated that inventive concepts can be applied to configure conical devices suitable for use in connection with a wide variety of cell culture apparatus. For example, inventive concepts are described herein with reference to multi-well plates such as 96-well culture plates, and others. However, the concepts disclosed herein can be readily applied to configure conical devices for other cell culture vessels, as desired.

Figure 3:
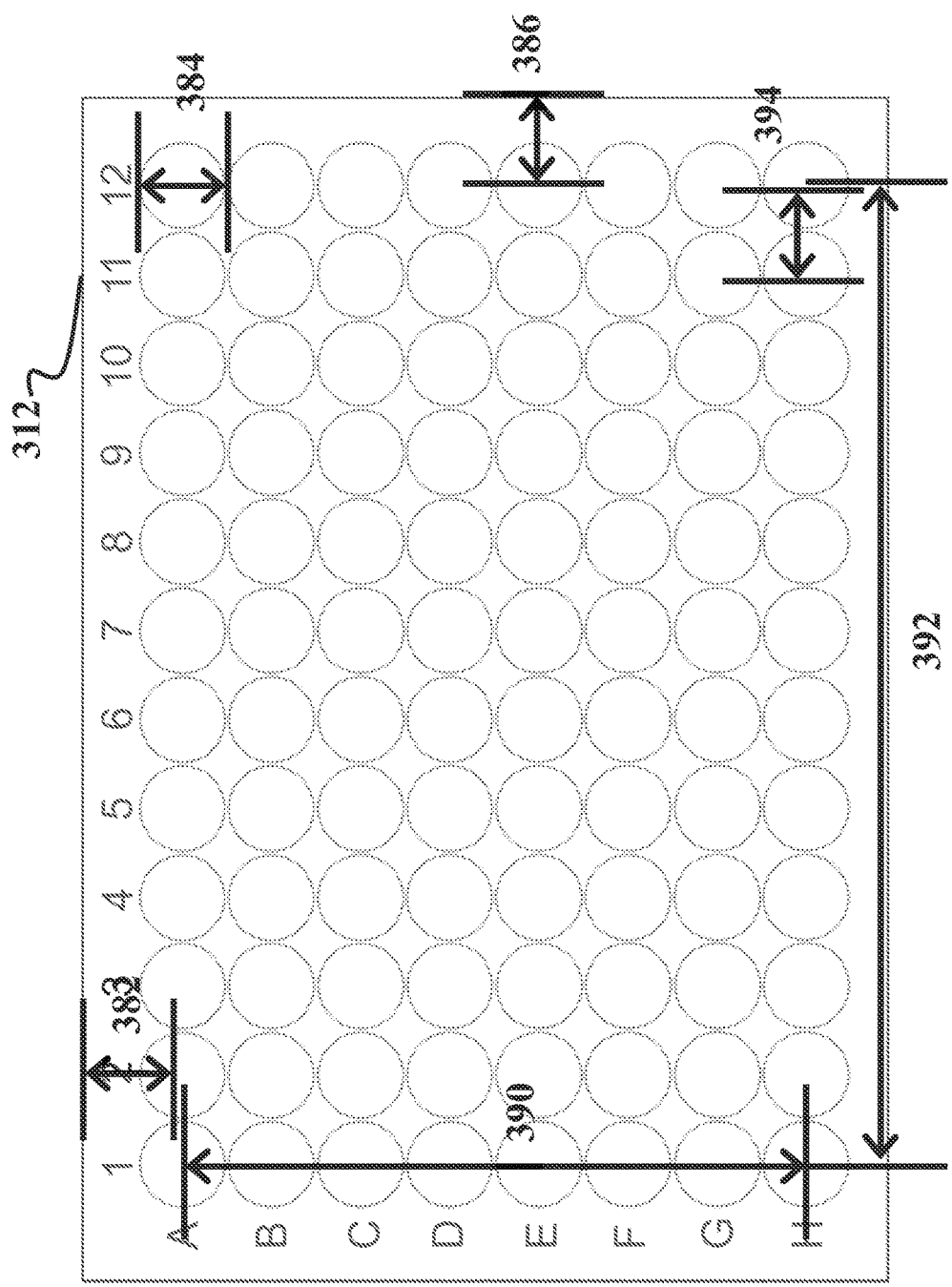
FIG. 3 is a schematic diagram top view of a commercially available 96-well cell culture plate and displays the average measurements of three commercially available 96-well cell culture plates.

The initial process for theoretically calculating a useful configuration for conical devices (including angles and sizes) to be placed into a common 96-well cell culture plate is described below. FIG. 3 illustrates the calculated average dimensions of a 96-well cell culture plate based on dimensions measured from three different commercially available culture plates: NUNCLON™ Delta F96 and NUNC™ Non-treated F96 microwell plates (Sigma-Aldrich. Milwaukee, Wis.); and Microtest Tissue Culture Plate F96 microwell plates (available from BD Falcon).

As illustrated in FIG. 3, a 96-well plate 312 will have a center-to-edge distance 382, typically about 9 mm on both sides of the plate. The top diameter 384 of an individual well of the plate is typically about 7 mm (+/−0.1 mm) and the bottom diameter of an individual well is approximately 6.4 mm (+/−0.2 mm). The center-to-edge distance 386 is typically about 11.8 mm on both sides of the plate. The center-to-center distance between the wells 394 is typically about 9.0 mm. The distance of the well bottom to the resting plane is typically about 3.2 mm, while the depth of individual wells of the plate is about 11.1 (+/−0.3 mm). The center-to-center row distance 392 is about 99 mm, while the center-to-center column distance 390 is about 63 mm.

Based on the information provided from FIG. 3, and assuming a conical device wall thickness of 0.5 mm, two types of conical devices for a standard 96-well cell culture plate were designed (see EXAMPLES 2, 3, 4, and 5 below).

The following guidelines can be made concerning the conical device construction for a 96-well plate. The diameter of the viewing aperture can be configured to retain a cell suspension and provide a suitable viewing aperture in accordance with inventive cell culture methods. In some aspects, the diameter of the viewing aperture in the apex of the conical device is preferably in the range of about 0.7 mm to about 1.9 mm, more preferably in the range of about 1.0 mm to about 1.4 mm. The upper cone diameter of the conical device can be configured to provide a suitable fit into a cell culture chamber (e.g., individual well of a cell culture plate) and provide access to the cell suspension during culture. In some aspects, the upper cone diameter of the conical device is preferably in the range of about 3.0 mm to about 8.4 mm, more preferably in the range of about 4.0 mm to about 5.5 mm. The height of the conical device, as measured along its vertical axis, is preferably in the range of about 8.5 mm to about 11.0 mm, more preferably in the range of about 9.0 mm to about 10.0 mm. The angle between the vertical axis and the side of the conical device near the viewing aperture is preferably in the range of about 9° to 89°, more preferably in the range of about 14° to 45°. The volume of the cell medium drop is preferably in the range of about 30 μL to 200 μL, more preferably about 30 to 35 μL during the process of forming cell aggregate(s), to about 60 to 100 μL once the aggregate(s) has (have) formed, thus improving ease of medium exchanges and increasing the volume of cell medium available to the 3D cell aggregate. The dimensions of the conical device can be scaled for other multi-well cell culture plates, including but not limited to 24- or 384-well cell culture plates by first determining the focal planes required for microscope viewing of a sample within a drop that is placed in a conical device.

Inventive concepts described herein can be utilized to determine suitable dimensions of a conical device of interest. For example, once a desired cell culture plate containing at least one well is selected, the dimensions of that well can be utilized in accordance with inventive concepts to determine suitable dimensions of a conical device. Generally speaking, the height of the conical device, as measured along its vertical axis, is typically long enough to allow the cells contained within the conical device to stay within the viewing range of a microscope, yet not so long as to touch the bottom of the cell culture well into which it is inserted. In a similar manner, the upper cone diameter, the angle between the vertical axis and the side of the conical device, and the diameter of the viewing aperture can be adjusted depending upon the dimensions of individual wells of a multi-well culture plate, as well as the desired volume of cell culture to be contained within the conical device.

Figure 4:
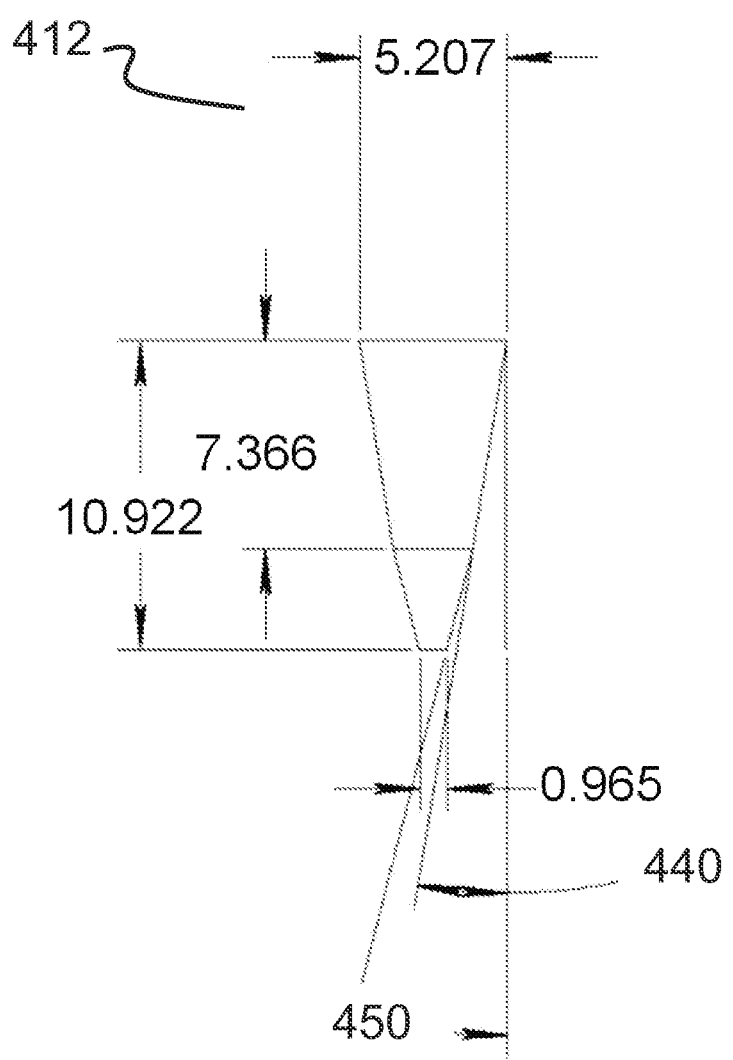
FIG. 4 is a schematic diagram cross-sectional view of a conical device designed for a standard 96-well cell culture plate (all dimensions are in mm unless otherwise marked)

One implementation of a conical device useful with standard 96-well cell culture plates in accordance with inventive aspects is illustrated in FIG. 4. Dimensions of the conical device are shown in mm. As illustrated, the conical device 412 has a first taper angle 440 and a second taper angle 450. With the particular dimensions illustrated in FIG. 4, the first taper angle 440 was 9.3° and the second taper angle 450 was 14.4°.

In many embodiments the conical device is opaque. In these embodiments the conical device can be white. It is believed that the opaque optical quality of the conical device can improve the viewing characteristics of the conical device. In many of these embodiments the conical device can be disposed or inserted into a light transparent multi-well cell culture container. Thus a cell culture disposed within the conical device can be viewed through the light transparent multi-well cell culture plate via a microscope as described herein.

Inventive conical devices can be assembled into kits for use in cell culture. Thus, in some implementations, kits are provided that include a cell culture vessel comprising a conical device having an inner surface being hydrophobic, and a frustum defining an open viewing aperture and a narrow end of the conical device; and a cell culture container comprising one or more chambers for cell culture.

Suitable cell culture vessels include all those described herein. In some implementations, the cell culture vessel includes a hydrophobic inner surface having a contact angle of at least 100 degrees, or at least 120 degrees, or at least 130 degrees, or at least 140 degrees. The hydrophobic surface can comprise particles (microparticles and/or nanoparticles as described herein). The hydrophobic surface can include at least about 50% wt particles. The conical device can be opaque and/or have a complex conical structure as described herein.

Illustrative cell culture containers for use in connection with kits can include any of those described herein. The cell culture container can include a lid or other removable cover. Additional components of the kit can include, for example, a cell culture medium (such as growth medium), a buffer solution, or the like.

In some implementations, methods for forming cell aggregates are provided, methods comprising steps of: (a) placing an amount of cell suspension into a cell culture vessel comprising a conical device having an inner surface being hydrophobic, and a frustum defining an open viewing aperture and a narrow end of the conical device, wherein the cell suspension comprises eukaryotic cells in medium either with or without serum; (b) allowing the formation of 3D cell aggregate(s) to occur within the cell suspension; and (c) observing over time the growth of 3D cell aggregate(s) in each cell suspension by employing a microscope for viewing up through the viewing aperture of the conical device.

In accordance with inventive concepts, cell suspension can be placed into the cell culture vessel through the base of the conical device (opposite the viewing aperture). The volume of cell culture can be in a range of about 30 µL to about 200 µL during the course of cell culture. The cell suspension can comprise any eukaryotic cells suitable for cell culture, as discussed elsewhere herein. Over time, the cell suspension medium will settle in the conical device and cell aggregates will form within the cell suspension. Growth of the cell aggregates can be observed through the viewing aperture of the conical device. An aqueous liquid can be placed in one or more chambers of the cell culture container. The cell culture container can be covered with a lid or other removable cover to provide a closed cell culture environment.

Some of the advantages of inventive concepts are further illustrated by the following examples. The particular materials, amounts and dimensions recited in the examples, as well as other conditions and details, should not be construed to unduly limit the present disclosure.

EXAMPLES

The present disclosure will be further explained in greater detail by the examples that follow; however, the scope of this disclosure is not construed to be limited by the scope of these examples.

High-impact polystyrene sheets (HIPS) with a thickness of 0.5 mm (0.020 inches) were purchased from Crown Plastics, Inc. (Plymouth, Minn.). Fluorescent acrylic, acrylonitrile-butadiene-styrene copolymer (ABS), and clear polyvinylchloride (PVC) sheets with a thickness of 0.25 mm (0.010 inches) were purchased from Walthers (Milwaukee, Wis.). Polypropylene (PP) sheets with a thickness of 0.76 mm (0.030 inches) were purchased from Plastics International (Eden Prairie, Minn.). These sheets were thermoformed using vacuum molding for the production of conical devices by Dave Hultman Design (Lindstrom, Minn.), and an end mill was then used to remove material at the apex of each conical device to form a smooth circular viewing aperture for each device, unless otherwise specified. Conical devices were singly cut out of the molded plastic sheets to be individually fit into the wells of a 96-well culture plate. Coupons approximately 1 $cm^2$ in area were cut from flat excess plastic.

The following procedure was used to prepare and coat each conical device or coupon evaluated in the examples unless otherwise specified. Conical devices or coupons were cleaned prior to coating using the following protocol: (1) rinsing with two sequential 30-second washes of isopropanol and n-hexane, respectively; and (2) blowing dry using bottled air, then further drying for at least two hours at lab ambient conditions. Each conical device or coupon was then coated by placing the conical device or coupon in a scintillation vial containing the desired coating solution or dispersion and gently inverting the vial and its contents repeatedly for 30 seconds. The coated devices were allowed to dry for at least two hours at room temperature and then were rinsed using a 30-second water wash. Residual water was removed using bottled air, and the conical devices or coupons were allowed to dry for at least one hour at room temperature before subsequent evaluation or experimentation.

Single conical devices were placed into a standard 96-well culture plate (NUNC™ Nontreated F96 microwell plate, Sigma-Aldrich, Milwaukee, Wis.), unless otherwise specified. Immediately before each cell culture experiment, the 96-well cell culture plate containing the conical devices was sterilized for 5 minutes on each side (10 minutes in total) using UV radiation (CL-1000 Ultraviolet Crosslinker, available from UVP; wavelength range of 250-400 nm with a peak at 254 nm; 6.5 mM/$cm^2$). The 96-well culture plate containing the conical devices was then transferred to the cell culture hood after sterilization was complete.

Example 1

White HIPS coupons were coated with two different polymers, both with and without the presence of nanoparticles to evaluate water contact angles. Two coupons were coated with polyisobutylene (PIB): one coupon, "PIB-coated," was coated with a 10 mg/mL PIB (90:10 mixture of Aldrich PIB $M_w$ 50 K:BASF Oppanol B PIB, $M_w$ 4 million, available from Aldrich, Milwaukee, Wis.; and BASF Corporation, Wilmington, Del., respectively) solution in n-hexane, and the other coupon, "PIB/Tex1-coated," was coated with a dispersion in n-hexane of 10 mg/mL PIB (90:10 mixture of Aldrich PIB $M_w$ 50K:BASF Oppanol B PIB, $M_w$ 4 million, available from Aldrich, Milwaukee, Wis.; and BASF Corporation, Wilmington, Del., respectively) and 12 mg/mL CABOT CAB-O-SIL™ TS-530 fumed silica nanoparticles (Cabot Corporation, Boston, Mass.). Two other coupons were coated with hydrophobic fluorinated copolymer: one coupon, "F8H2A-coated," was coated with a 10 mg/mL fluorinated copolymer (1H,1H,2H, 2H-perfluorodecyl acrylate:methyl acrylate ratio 10:90 F8H2A:MA) (Innovative Surface Technologies, St. Paul, Minn.) solution in acetonitrile; and the other coupon, "F8H2A/Tex1-coated," was coated with a dispersion of 10 mg/mL F8H2A:MA and 12 mg/mL CABOT CAB-O-SIL™ TS-530 fumed silica nanoparticles in acetonitrile.

Coupons were cleaned and subsequently coated using the previously described protocols at the beginning of the "EXAMPLES" section. Contact angles were determined using a Micro Vu 400 goniometer, air displacement pipette (1-20 microliter) and a 10-microliter drop of deionized water. The average values of 6 drops for all coatings except for PIB/Tex-coated coupon (average value of 3 drops) are reported in Table 1.

TABLE 1

Water contact angle for coated coupons.

| Coupon | Water contact angle (in degrees) |
|---|---|
| PIB-coated | 90 ± 6 |
| PIB/Tex1-coated | 149 ± 6 |
| F8H2A-coated | 104 ± 8 |
| F8H2A/Tex1-coated | 128 ± 6 |

The water contact angle for the PIB/Tex1-coated coupon was challenging to obtain since it was very difficult to place a water drop on the surface. The water drop preferred to hang from the pipette tip instead of resting on the coated surface and if a drop of water could be forced to fall from the tip of the pipet it would completely roll off of the flat coated surface. The PIB/Tex1-coated surface was not wetted by water and was superhydrophobic. The textured PIB/Tex1-coated surface had a higher contact angle than the non-textured PIB-coated surface.

The textured F8H2A/Tex1-coated surface was not superhydrophobic since it was very easy to place the water drop onto the surface and when the water drop was shaken off of the surface a wet spot remained at the drop location. The textured F8H2A/Tex1-coated surface had a higher water contact angle than the non-textured F8H2A-coated surface.

Example 2

Conical devices having similar dimensions to the conical device illustrated in FIG. 4 were vacuum formed and used in order to determine whether the position of an aqueous drop inside a conical device would be located at a suitable focal distance when examined by an inverted microscope to ensure proper viewing of the drop and its contents for cell culture experiments and for taking digitized microscope images (LEICA™ DM IL LED microscope, used with a LEICA™ DFC 400 12V, 200 mA digitizer and LEICA™ Application Suite software; available from Leica Microsystems, Buffalo Grove, Ill.).

Three conical devices were singly cut out of the molded 0.5-mm-thick molded white HIPS sheet in order to individually fit into the wells of a commercially available 96-well cell culture plate. Each device was used as a separate experiment. Conical devices were cleaned and subsequently coated using the previously described protocols at the beginning of the "EXAMPLES" section.

Figure 5:
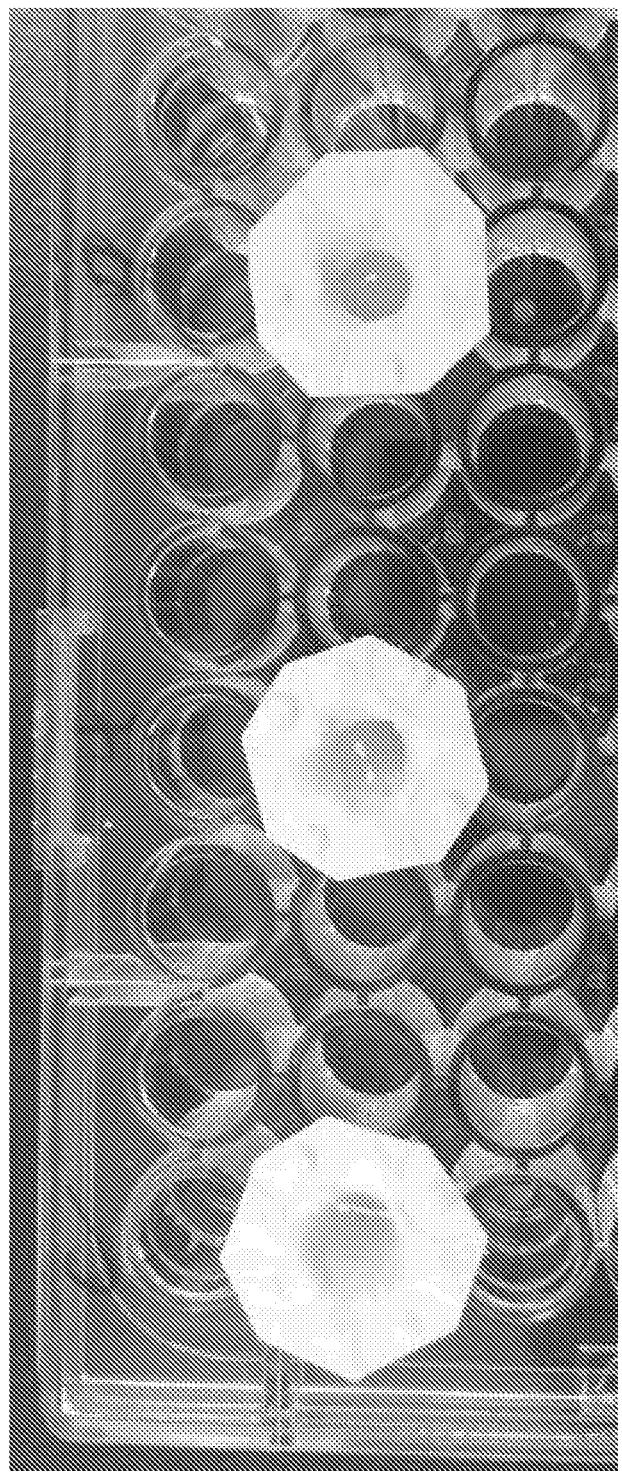
FIG. 5 is a photograph of vacuum-formed polystyrene conical devices in a standard 96-well culture plate each holding a drop (50 μL) of an aqueous dispersion of DYNA-BEADS™: A) uncoated device; B) 4 mg/mL PIB/Tex2-coated device; C) 10 mg/mL PIB/Tex2-coated device.

FIG. 5 illustrates the vacuum formed polystyrene conical devices in a standard 96-well culture plate, each conical device holding a drop (50 µL) of an aqueous dispersion of DYNABEADS™. As illustrated in FIG. 5, one conical device was left uncoated (Device A). The other two conical devices were coated with two different concentrations of a superhydrophobic coating dispersion: Device B (4 mg/mL PIB/Tex2-coated), was coated with a dispersion in n-hexane of 4 mg/mL PIB (90:10 mixture of Aldrich PIB $M_w$ 50 K:BASF Oppanol B PIB, $M_w$ 4 million) and 4.8 mg/mL CABOT CAB-O-SIL™ TS-720 fumed silica nanoparticles (Cabot Corporation, Boston, Mass.); and Device C (10 mg/mL PIB/Tex2-coated) was coated with a dispersion in n-hexane of 10 mg/mL PIB (90:10 mixture of Aldrich PIB $M_w$ 50K:BASF Oppanol B PIB, $M_w$ 4 million) and 12 mg/mL CABOT CAB-O-SIL™ TS-720 fumed silica nanoparticles.

Figure 6:
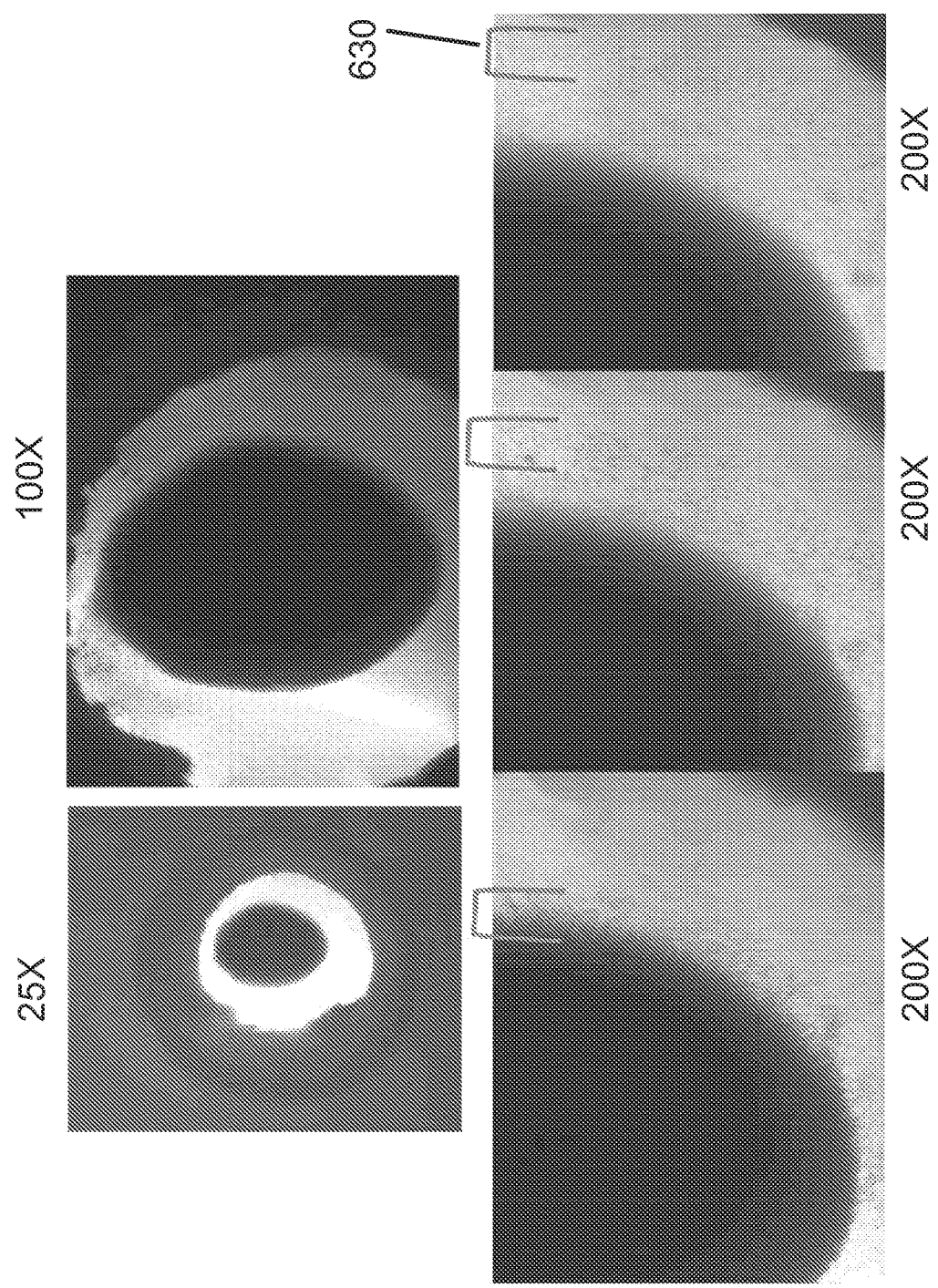
FIG. 6 are optical micrographs of a textured hydrophobic conical device for a 96-well plate holding a 50-μL aliquot of an aqueous solution of 1-μm MyOne Carboxylic Acid Dynabead® microparticles (the brackets denote different focal planes within the sample accessible to a standard inverted microscope in which microparticles are in the process of aggregating at the bottom of the drop meniscus)

To provide a visual medium for the microscope, a 50-µL drop consisting of a 0.1-mg/mL aqueous dispersion of MyOne™ Carboxylic Acid DYNABEADS™ (available from Life Technologies, Grand Island, N.Y.) was placed into each of the three conical devices. FIG. 6 shows optical micrographs taken of the microparticle-containing drops located above the apex of the textured hydrophobic conical device. Magnification is indicated on each image, and the brackets 630 denote different focal planes within the sample accessible to a standard inverted microscope. FIG. 6 shows the DYNABEADS™ were in the process of aggregating at the bottom of the drop meniscus during the time of this experiment within the 10 mg/mL PIB/Tex2-coated conical device. Similar results were observed using the 4 mg/mL PIB/Tex2-coated conical device (data not shown). These results demonstrate that a standard inverted microscope (Leica DM IL LED) is able to focus on various focal planes (represented by the brackets 630 in FIG. 6) in an aqueous sample within a textured hydrophobic conical device. Thus, this conical device with a textured hydrophobic surface permits access to various focal planes within the liquid drop in the device using a standard inverted microscope.

Example 3

Three textured hydrophobic conical devices having similar dimensions to the conical device illustrated in FIG. 4 were evaluated for utility and non-cytotoxicity in monitoring the growth of 3D eukaryotic cell aggregate(s) in drops containing eukaryotic cells suspended in culture medium. Bovine aortic endothelial (BAEC) cells were used in this experiment.

Conical devices were cleaned and subsequently coated using the previously described protocols at the beginning of the "EXAMPLES" section. One conical device was left uncoated.

The other two conical devices were coated using two different types of nanoparticles in a dispersion in n-hexane with polyisobutylene (PIB): one device, "PIB/Tex1-coated," was coated with a dispersion in n-hexane of 10 mg/mL PIB (90:10 mixture of Aldrich PIB $M_w$ 50K:BASF Oppanol B PIB, $M_w$ 4 million) and 12 mg/mL CABOT CAB-O-SIL™ TS-530 fumed silica nanoparticles, and the other device, "PIB/Tex2-coated," was coated with a dispersion in n-hexane of 10 mg/mL PIB (90:10 mixture of Aldrich PIB $M_w$ 50 K:BASF Oppanol B PIB, $M_w$ 4 million) and 12 mg/mL CABOT CAB-O-SIL™ TS-720 fumed silica nanoparticles.

BAEC cells growing in flasks were trypsinized and resuspended in growth medium (DMEM containing 10% FBS). A 35-µL aliquot of a BAEC cell suspension containing ~1100 cells/device was then added to each of the eight modified conical devices in the 96-well plate using a standard micropipette. A 250-µL aliquot of DMEM containing 10% FBS was added to each of the outside wells of a 96-well plate (36 wells in total) to maintain a humid environment within the covered 96-well plate. The cell suspension in the devices/plate was incubated at 37° C., 5% $CO_2$ and monitored periodically for eight days. Cell aggregation was observed after 2, 6, and 8 days of cell culture and is shown in FIG. 7.

Figure 7:
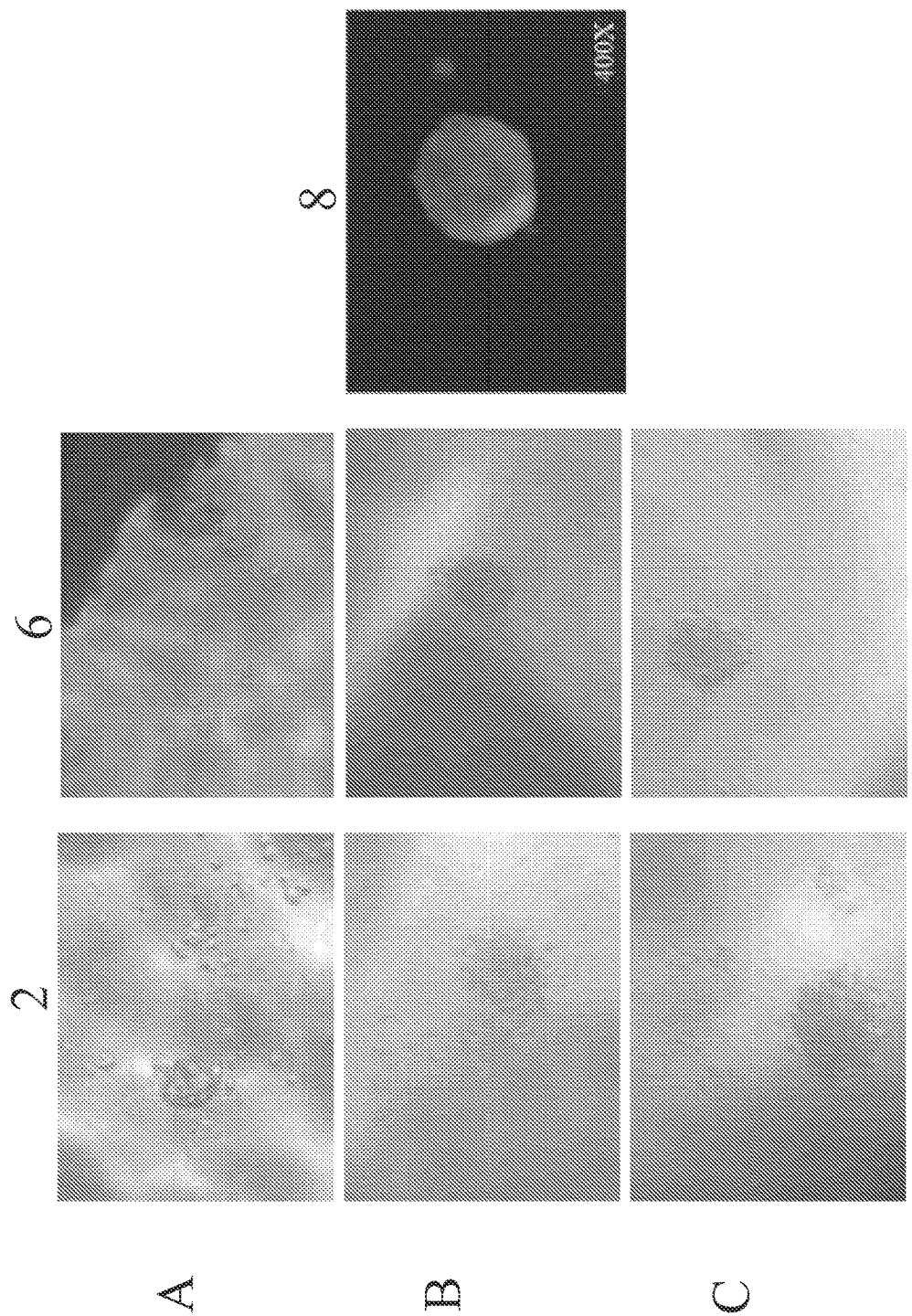
FIG. 7 are optical micrographs of BAEC cell aggregates (~1100 cells) in an uncoated polystyrene conical device (top two panels, Row A), a PIB/Tex1-coated polystyrene conical device (middle two panels, Row B), and a PIB/Tex2-coated polystyrene conical device (bottom two panels, Row C) after 2 and 6 days of cell culture in DMEM with 10% FBS. The panel on the right shows the live/dead assay after eight days of cell culture for the BAEC aggregate in the PIB/Tex1-coated polystyrene conical device (magnification 200×). The number of days at which each micrograph was taken is indicated above each column.

In FIG. 7, the uncoated polystyrene conical device is shown in Row A. PIB/Tex1-coated insert is shown in Row B, and the PIB/Tex2-coated insert is shown in Row C. Images are shown for Days 2, 6 and 8. Magnification is 200×. As illustrated in FIG. 7, before Day 6, the multiple 3D cell aggregates forming in the uncoated device at 37° C., 5% $CO_2$ had moved over to the side wall of the device and pinned to the uncoated polystyrene surface. Single 3D cell aggregates in both the PIB/Tex1- and the PIB/Tex2-coated conical devices remained positioned in or near the middle throughout the eight-day experiment and did not attach or pin to the walls of the textured hydrophobic device.

After eight days of culture, cells were subjected to a live/dead cell assay. Because the serum in the DMEM medium with 10% FBS quenches fluorescence, cell aggregate(s)/suspension were removed from the devices and placed into separate sterile 0.75-mL centrifuge tubes. A 50-µL aliquot of sterile phosphate buffered saline solution (PBS) was added to each tube, and after 2-3 minutes, a 30-µL aliquot of medium/PBS was removed from the top of the medium in each tube without disturbing the aggregate(s) on the bottom of the tube. This wash was repeated one more time and the remaining solutions were added to three separate wells in a 96-well cell culture plate, respectively. A 2-µL aliquot of a 2-mM ethidium homodimer-1 (EthD-1) solution in 1:4 (v/v) $DMSO:H_2O$ and 1 µL of a 4-mM calcein AM solution in anhydrous DMSO was added to 997 µL of sterile PBS for a final concentration of ~4 µM EthD-1/~4 µM calcein AM for a live/dead viability/cytotoxicity assay (Live/Dead Viability/Cytotoxicity Kit, Cat#L3224, obtained from Invitrogen, Grand Island, N.Y.). EthD-1, which cannot permeate the membranes of viable cells, increases 40-fold in fluorescence upon binding to nucleic acids in cells with damaged cell membranes and produces a red fluorescence in dead cells ($\lambda_{ex}$~495 nm/$\lambda_{em}$~635 nm). Calcein AM, which is able to permeate the cell membrane, produces a uniform green fluorescence in live cells ($\lambda_{ex}$~495 nm/$\lambda_{em}$~515 nm). A 50-µL aliquot of this ~4 µM EthD-1/~4 µM calcein AM stock solution was added to each of the three wells containing aggregate(s). The solutions in the 96-well plate were incubated for 0.5-1 hours at 37° C., 5% $CO_2$ and then analyzed using the Leica DM IL LED inverted microscope with a Leica DFC 400 12V/200 mA digitizer and the Leica Application Suite.

Results of the live/dead assay for the PIB/Tex1-coated device are shown in the right panel (labeled Day 8) of FIG. 7. Briefly, Row B Day 8 of FIG. 7 shows that approximately 98% of the cells were live (green) cells whereas approximately only 2% of the cells were dead (red) cells in the aggregate. Therefore, the live/dead assay indicates that the textured hydrophobic coatings are not toxic to the cells.

Several important observations resulted from this experiment: the textured hydrophobic coatings proved to be (1) bioinert and (2) non-cytotoxic to the cells while (3) preventing cell attachment or pinning to the interior walls of the textured hydrophobic conical device. Furthermore, (4) BAEC cells formed a single, tight spherical 3D cell aggregate in both PIB/Tex1-coated and PIB/Tex2-coated textured hydrophobic conical devices compared to the multiple loose aggregates present in the uncoated devices.

Example 4

Figure 8:
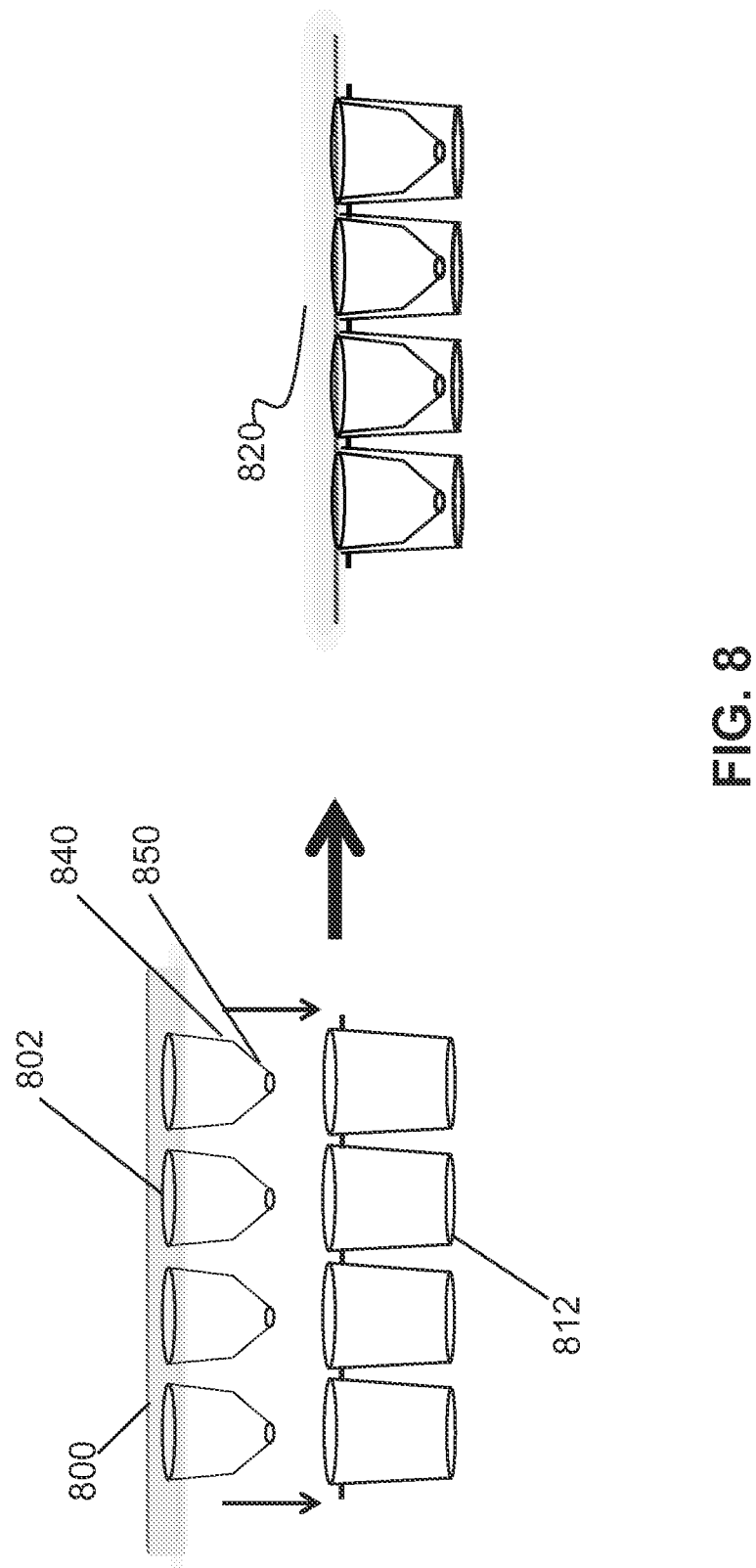
FIG. 8 is a schematic diagram of a molded sheet containing conjoined conical devices of a modified conical geometry fitting into a standard 96-well plate for 3D cell culture.

The textured hydrophobic devices were evaluated for their long-term culture efficiency. A modified conical geometry, shown in FIG. 9, was also evaluated during this experiment. In this geometry, the cone angle at the apex has been expanded to ~45° to the vertical. In this illustration, the first taper angle 840 is approximately 5° to the vertical, and the second taper angle 850 is approximately 45° to the vertical; the second taper angle 850 is about 40° greater than the first taper angle 840. FIG. 8 illustrates a molded sheet containing conjoined modified conical devices of FIG. 9 congruently fitting into a multi-well cell culture plate.

As illustrated in FIG. 8, a modified cell culture vessel array 800 includes modified conical devices 802 that can be inserted into wells 812 of a multi-well plate. The modified conical devices 802 include a first taper angle 840 and a second taper angle 850. A cell culture assembly 820 is formed when the modified cell culture vessel array 800 is inserted into wells 812 of a multi-well plate.

Figure 9:
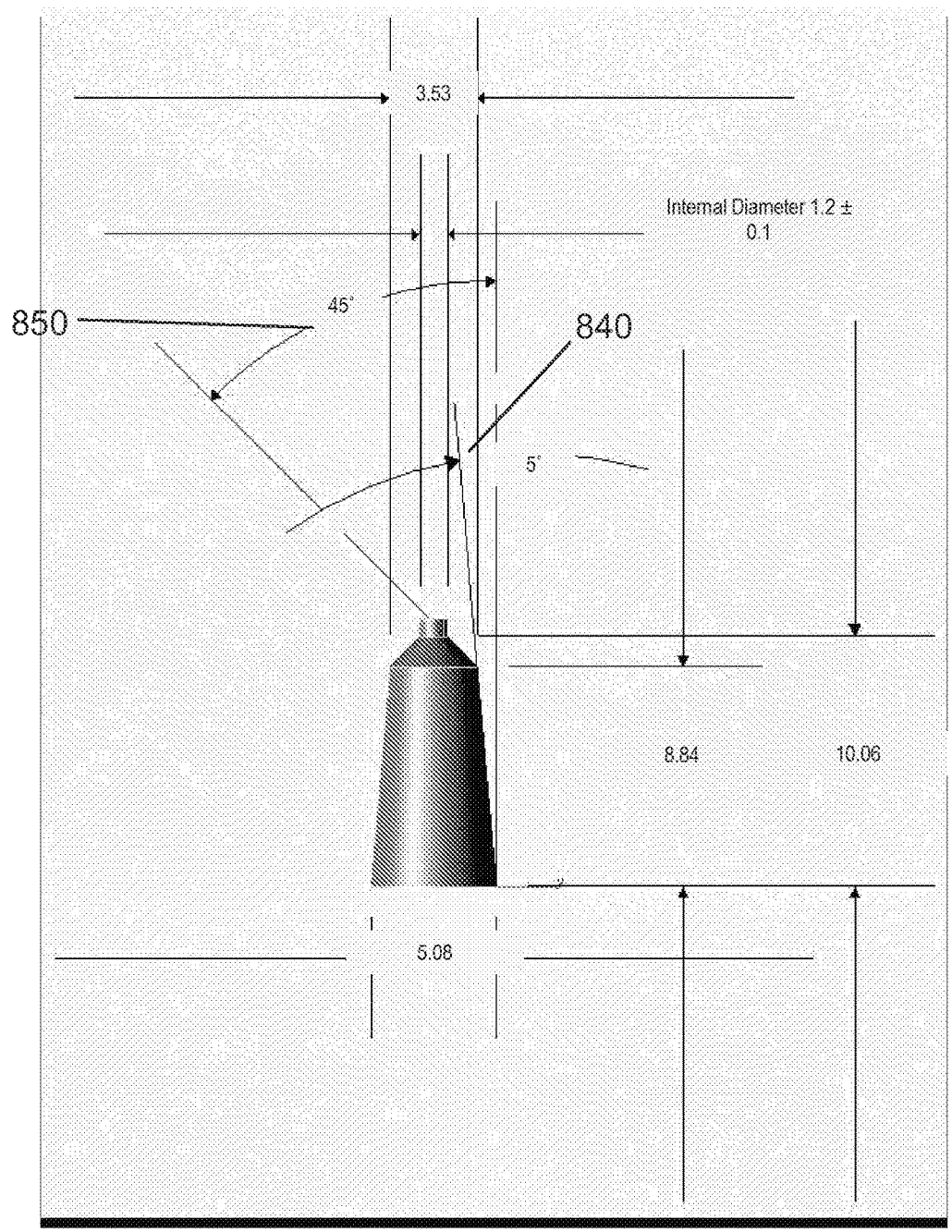
FIG. 9 is a schematic diagram of a modified conical device designed for a standard 96-well cell culture plate (magnification 100×; all dimensions are in mm unless otherwise marked)

Five modified conical devices having similar dimensions to the schematic in FIG. 9 with viewing apertures were singly cut out of molded 0.5-mm thick molded polystyrene (HIPS) sheets in order to individually fit into the wells of a commercially available 96-well cell culture plate.

Modified conical devices were cleaned and subsequently coated using the previously described protocols at the beginning of the "EXAMPLES" section. One modified conical device was left uncoated. The other four modified conical devices were coated with two different polymers, both with and without the presence of nanoparticles. One set of devices (2) was coated with a PIB homopolymer-based solution or dispersion: one device, "PIB-coated," was coated with a 10 mg/mL PIB (90:10 mixture of Aldrich PIB $M_w$ 50K:BASF Oppanol B PIB, $M_w$ 4 million) solution in n-hexane, and the other device, "PIB/Tex1-coated," was coated with a dispersion in n-hexane of 10 mg/mL PIB (90:10 mixture of Aldrich PIB $M_w$ 50K:BASF Oppanol B PIB, M 4 million) and 12 mg/mL CABOT CAB-O-SIL™ TS-530 fumed silica nanoparticles. The other set of devices (2) was coated with a hydrophobic fluorinated copolymer-based solution or dispersion: one device, "F8H2A-coated," was coated with a 10 mg/mL fluorinated copolymer (1H, 1H,2H,2H-perfluorodecyl acrylate:methyl acrylate ratio 10:90 F8H2A:MA) (Innovative Surface Technologies, St. Paul, Minn.) solution in acetonitrile, and the other device, "F8H2A/Tex1-coated," was coated with a dispersion in acetonitrile of 10 mg/mL F8H2A:MA (10:90) and 12 mg/mL CABOT CAB-O-SIL™ TS-530 fumed silica nanoparticles.

HeLa cells growing in flasks were trypsinized and resuspended in growth medium (MEM containing 10% FBS). A 35-µL aliquot of a HeLa cell suspension containing ~1100 cells/device was then added to each of the eight modified conical devices in the 96-well plate using a standard micropipette. A 250-µL aliquot of MEM containing 10% FBS was added to each of the outside wells of a 96-well plate (36 wells in total) to maintain a humid environment within the covered 96-well plate. The cell suspension in the devices was incubated at 37° C., 5% $CO_2$ and monitored periodically for ten days. Cell suspensions were observed after 1, 2, 3, 6, 8, and 10 days of cell culture and are shown in FIGS. 10, 11, 12, 13, and 14. For each of these figures, micrograph images were taken at Days 1, 2, 3, 6, 8 and 10 (as indicated above each image), and magnification was 100×.

Figure 10:
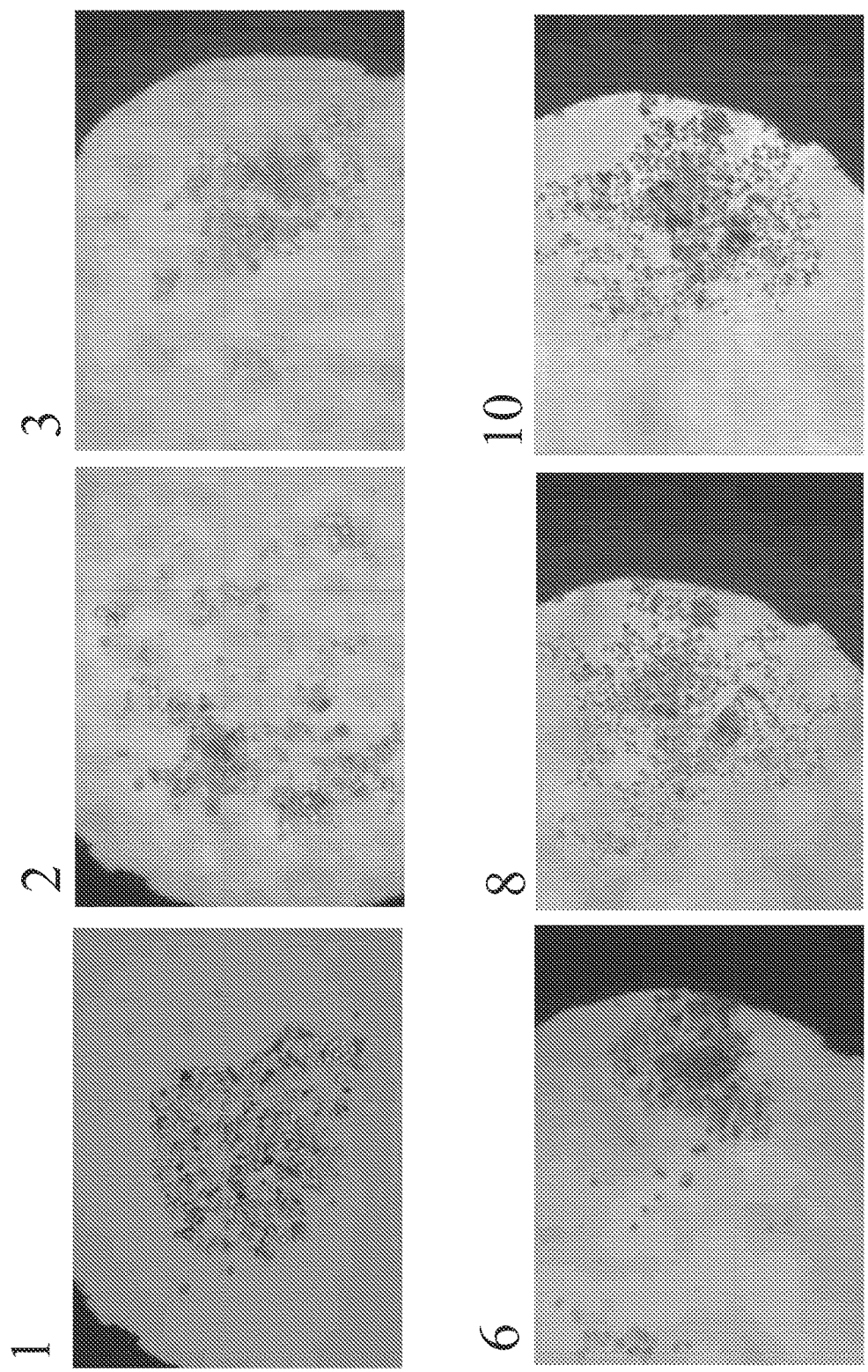
FIG. 10 are optical micrographs of HeLa cells (~1100 cells per device) in uncoated polystyrene modified cone devices over a ten-day 3D growth period. The number of days at which each micrograph was taken is indicated above the respective image.
Figure 11:
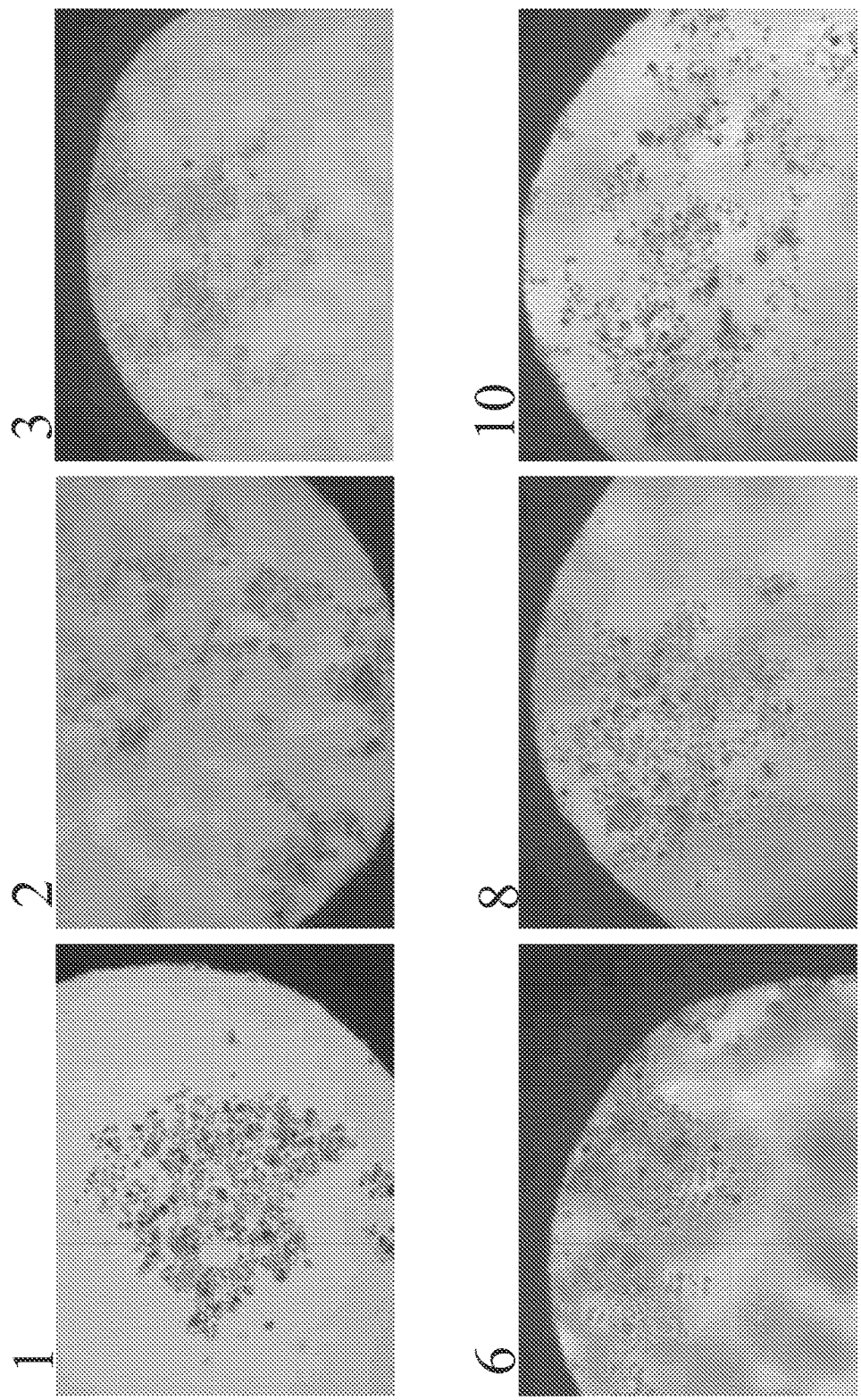
FIG. 11 are optical micrographs of HeLa cells (~1100 cells per device) in PIB-coated polystyrene modified cone devices over a ten-day 3D growth period (magnification 100×). The number of days at which each micrograph was taken is indicated above the respective image.
Figure 12:
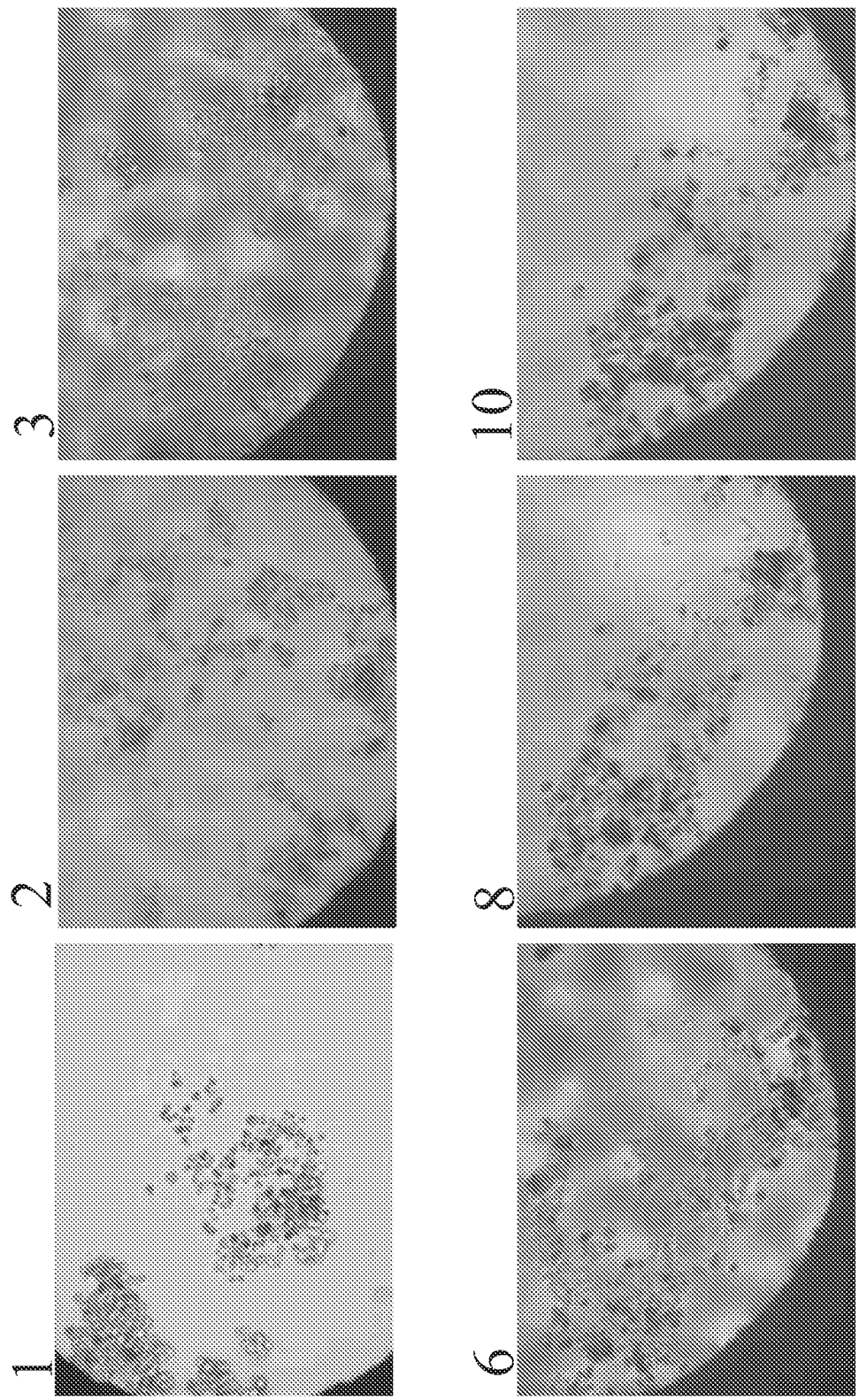
FIG. 12 are optical micrographs of HeLa cells (~1100 cells per device) in F8H2A-coated polystyrene modified cone devices over a ten-day 3D growth period (magnification 100×). The number of days at which each micrograph was taken is indicated above the respective image.
Figure 13:
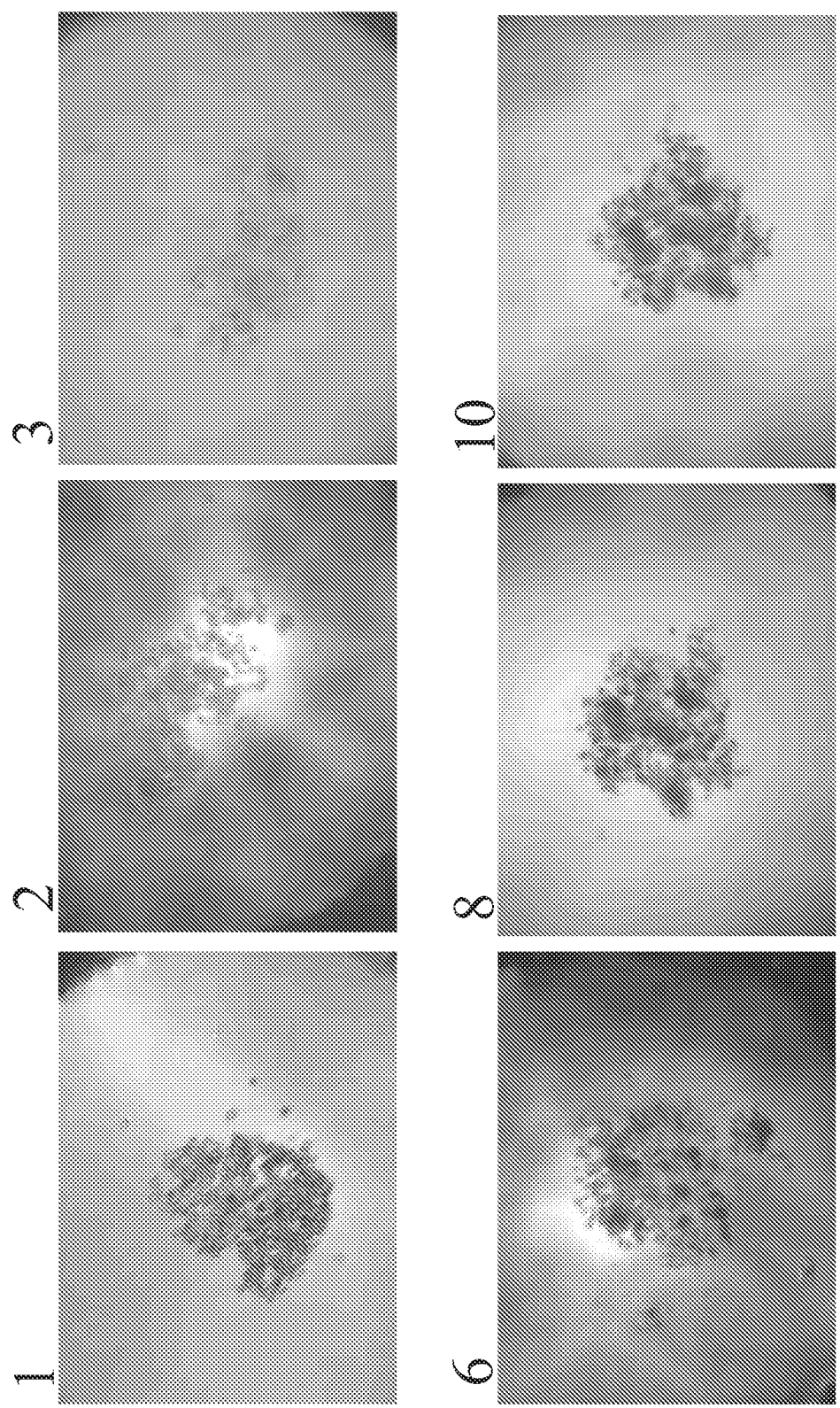
FIG. 13 are optical micrographs of HeLa cells (~1100 cells per device) in PIB/Tex1-coated polystyrene modified cone devices over a ten-day 3D growth period (magnification 100×). The number of days at which each micrograph was taken is indicated above the respective image.
Figure 14:
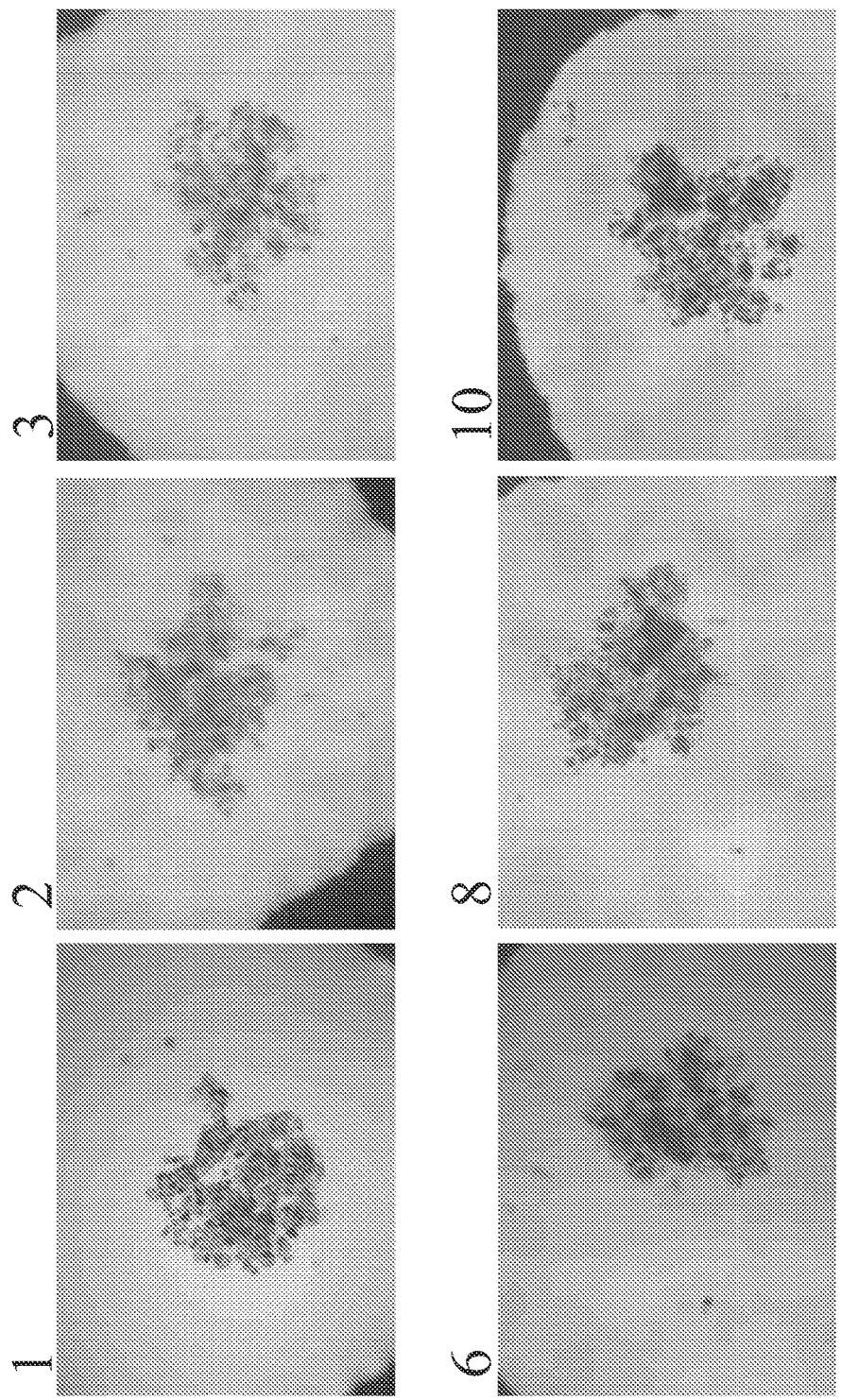
FIG. 14 are optical micrographs of HeLa cells (~1100 cells per device) in F8H2A/Tex1-coated polystyrene modified cone devices over a ten-day 3D growth period (magnification 100×). The number of days at which each micrograph was taken is indicated above the respective image.

FIG. 10 shows micrographs of the HeLa cell aggregates (approximately 1100 cells per device) present in the uncoated polystyrene modified conical device over a ten-day 3D growth period. FIG. 11 shows micrographs of the HeLa cell aggregates present in the PIB-coated polystyrene modified conical device (coated with PIB homopolymer alone without the addition of nanoparticles). FIG. 12 shows micrographs of the HeLa cell aggregates present in the F8H2A-coated polystyrene modified conical device (coated with a 10:90 mixture of F8H2A:MA alone without the addition of nanoparticles). FIG. 13 shows micrographs of the single 3D cell aggregate present in the PIB/Tex1-coated polystyrene modified conical device. FIG. 14 shows micrographs of the single 3D cell aggregate present in the F8H2A/Tex1-coated polystyrene modified conical device.

From examining the micrographs in FIGS. 10, 11, and 12, using uncoated polystyrene devices or devices coated with polymer alone (i.e., without the presence of nanoparticles) resulted in the formation of multiple loose HeLa cell aggregates. The uncoated and polymer-coated devices failed to prevent the pinning of the cells/aggregate(s) to the sides of the device as early as the second day of culture.

From examining the micrographs in FIGS. 13 and 14, using PIB/Tex1-coated or F8H2A/Tex1-coated modified conical devices (i.e., nanoparticles were present in the coatings) resulted in the formation of well-formed, single 3D spherical HeLa cell aggregates while preventing pinning of the cells/aggregates to the sides of the device throughout the course of the ten-day experiment.

Figure 15:
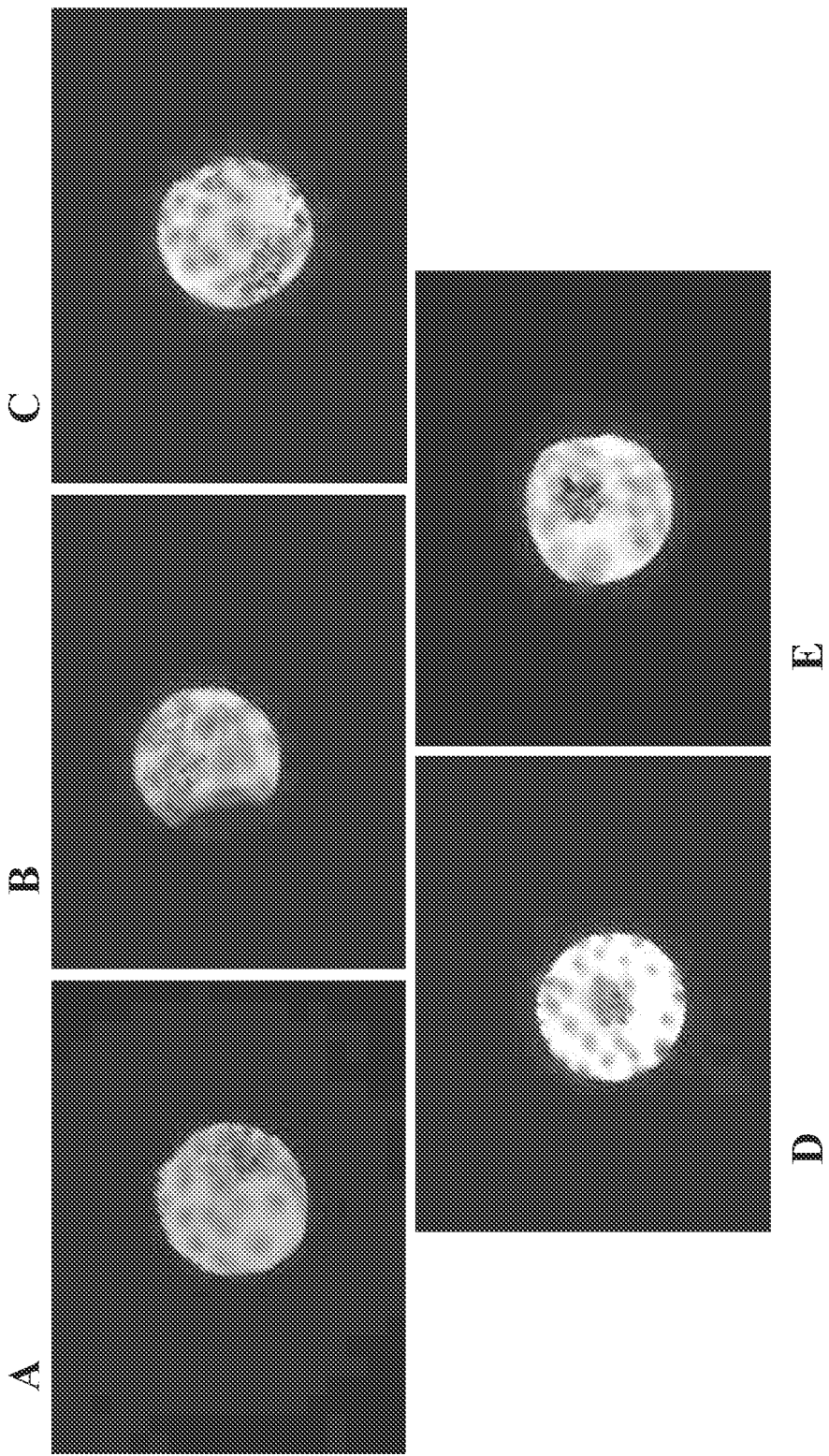
FIG. 15 are optical micrographs of HeLa cells (~1100 cells per device) in uncoated and various coated polystyrene modified cone devices after a ten-day 3D growth period (magnification 25×)

FIG. 15 shows the location of HeLa cell aggregate(s) on Day 10 within both uncoated and coated modified conical devices. Magnification is 25×. The following are depicted in FIG. 15:

| | |
|---|---|
| A | Uncoated polystyrene |
| B | PIB-coated polystyrene |
| C | F8H2A-coated polystyrene |
| D | PIB/Tex1-coated polystyrene |
| E | F8H2A/Tex1-coated polystyrene |

The single 3D HeLa cell aggregates in the PIB/Tex1- or F8H2A/Tex1-coated textured hydrophobic modified conical devices do not appear to adhere to the sides of the conical device whereas the aggregates in the uncoated, PIB-, and F8H2A-coated modified conical devices lacking nanoparticles appear to be attracted or pinned to the sides of the conical device.

The textured hydrophobic devices were evaluated for their long-term culture efficiency. A modified conical device geometry with two different types of textured hydrophobic coatings was tested for over 20 days with two different eukaryotic cell lines: HeLa cell aggregate(s) were tested in F8H2A/Tex1-coated modified conical devices and BAEC cell aggregrate(s) were tested in PIB/Tex1-coated modified conical devices. Both the HeLa and BAEC cells/aggregate(s) in their respective growth mediums remained within the modified conical devices for the entire growth period and were not spontaneously or otherwise released into the bottom of the 96-well plate during for over 20 days.

Figure 16:
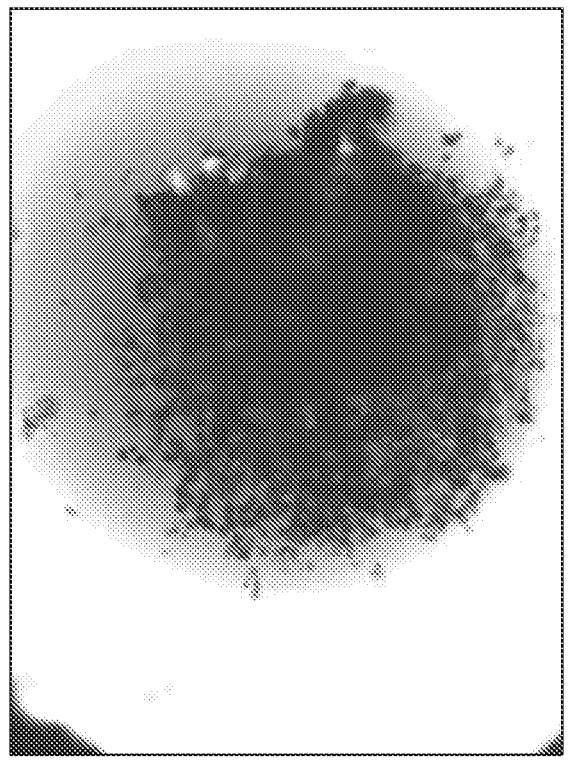
FIG. 16 are optical micrographs of HeLa cells (~1500 cells per device) in F8H2A/Tex1-coated modified cone devices after a 21-day 3D growth/culture period.
Figure 16:
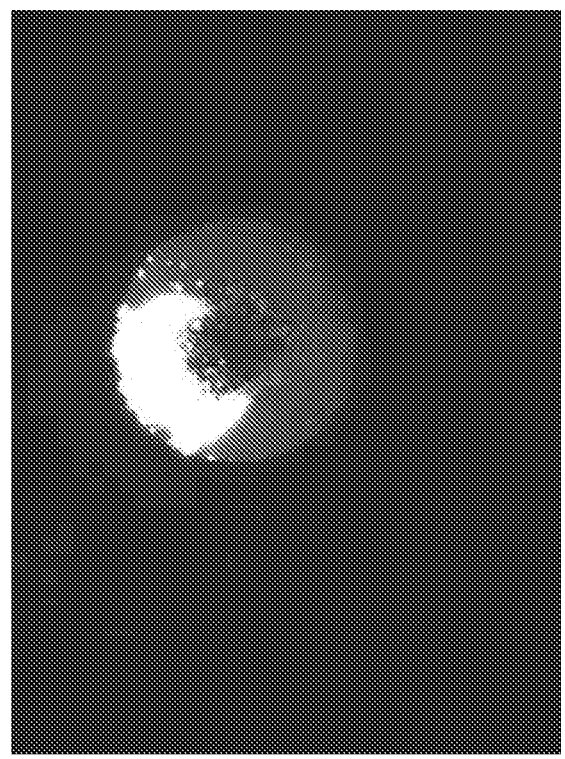

FIG. 16 shows a single, large HeLa cell aggregate (initial seeding density was ~1500 cells) in an F8H2A/Tex1-coated modified conical device. Magnification of the left image was 25×, while magnification of the right image was 100×. As shown, the cell aggregate remained clustered in the middle of the device for 22 days, demonstrating the robustness of the textured hydrophobic coating. Therefore, the combination of device geometry and the long-term durability of the textured hydrophobic surface provides an efficient system for the generation and maturation of cell aggregates in long-term cultures.

Example 5

Acrylic, acrylonitrile-butadiene-styrene copolymer (ABS), clear polyvinyl chloride (PVC), and polypropylene (PP) were used as additional plastics for testing modified conical devices both with and without a textured hydrophobic coating. Two modified conical devices (of the design shown in FIG. 9) with viewing apertures were singly cut out of molded sheets of devices for each of the aforementioned plastics (eight devices in total). Modified conical devices were cleaned and subsequently coated using the previously described protocols at the beginning of the "EXAMPLES" section. One modified conical device made from each plastic was left uncoated (a total of 4 uncoated devices). The other four modified conical devices were coated with a dispersion of 10 mg/mL PIB (90:10 mixture of Aldrich PIB $M_w$ 50 K:BASF Oppanol B PIB, $M_w$ 4 million) and 12 mg/mL CABOT CAB-O-SIL™ TS-530 fumed silica nanoparticles (available from Cabot Corporation, Boston, Mass.) in n-hexane, henceforth denoted as "PIB/Tex1-coated."

HeLa cells growing in flasks were trypsinized and resuspended in growth medium (MEM containing 10% FBS). A 35-μL aliquot of a HeLa cell suspension containing ~1100 cells/device was then added to each of the eight modified conical devices in the 96-well plate using a standard micropipette. A 250-μL aliquot of MEM containing 10% FBS was added to each of the outside wells of a 96-well plate (36 wells in total) to maintain a humid environment within the covered 96-well plate. The cell suspension in the devices was incubated at 37° C., 5% $CO_2$ and monitored periodically for five days. Cell suspensions were observed after 1, 2, and 5 days of cell culture.

Figure 17:
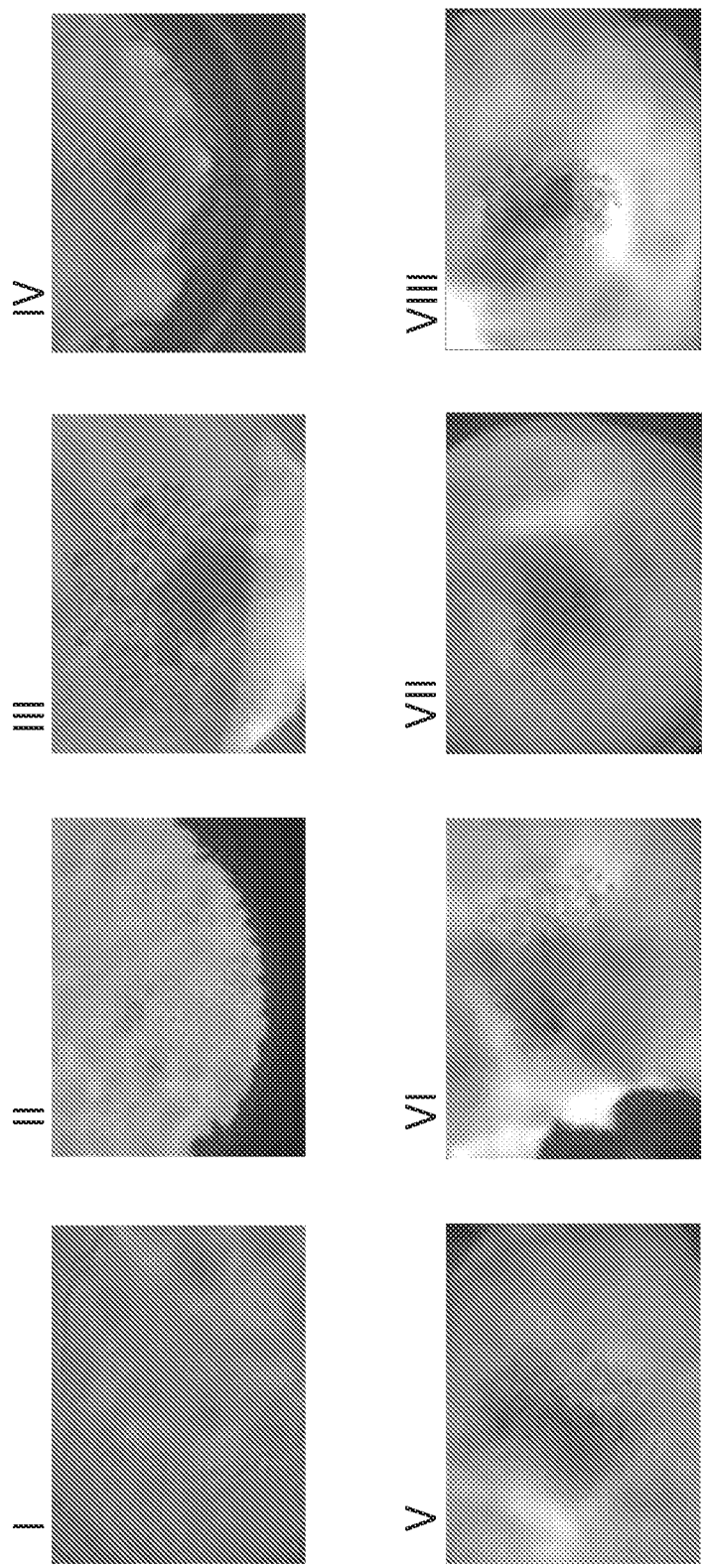
FIG. 17 are optical micrographs of HeLa cells (~1100 cells per device) in both uncoated and PIB/Tex1-coated acrylic, acrylonitrile-butadiene-styrene copolymer (ABS), polypropylene (PP), and polyvinylchloride (PVC) modified cone devices after five days of culture (magnification 100×)

FIG. 17 shows optical micrographs of HeLa cells in both uncoated and PIB/Tex1-coated ABS, PP and PVC modified conical devices after five days of culture. Magnification was 100×. The images included in FIG. 17 are as follows:

| | |
|---|---|
| I | Uncoated Acrylic |
| II | Uncoated ABS |
| III | Uncoated PP |
| IV | Uncoated PVC |
| V | PIB/Tex1-coated Acrylic |
| VI | PIB/Tex1-coated ABS |
| VII | PIB/Tex1-coated PP |
| VIII | PIB/Tex1-coated PVC |

The Images I, II, III and IV of FIG. 17 show that HeLa cell aggregate(s) in uncoated acrylic, ABS, and PVC modified conical devices were attracted or pinned to the device walls. Further, the uncoated PP modified conical device (Image III) failed (released its cell culture in medium to the bottom of the well below) before the fifth day of growth. Images V, VI, VII and VIII of FIG. 17 show that HeLa cells formed spherical aggregate(s) in the middle of all four PIB/Tex1-coated modified conical devices. From this experiment, it was observed that a textured hydrophobic coating can be used in conjunction with thermoformable plastics in addition to polystyrene, specifically acrylic, ABS, PP, and PVC, to produce the textured hydrophobic modified conical device.

Example 6

White, high-impact polystyrene sheets (HIPS) with a thickness of 0.5 mm (0.020 inches) were purchased from Crown Plastics, Inc. (Plymouth, Minn.). These sheets were thermoformed using vacuum molding for the production of a 6×10 tray of conical devices similar to FIG. 9 by PN Products (Scandia, Minn.). A metal punch and hammer was then used to remove material at the apex of each conical device to form a smooth circular viewing aperture for each device. The diameter of the viewing apertures in the apex of the conical devices is in the range of about 1.0 mm to 1.2 mm.

The conical devices were cleaned prior to coating using the following protocol: (1) rinsing with two sequential 30-second washes of isopropanol and n-hexane, respectively; and (2) blowing dry using bottled air, then further drying for at least two hours at lab ambient conditions. The tray of conjoined conical devices, "PIB/Tex3-coated," was then coated by placing the tray in a 250-mL amber vial containing a dispersion in n-hexane of 10 mg/mL PIB (90:10 mixture of Aldrich PIB $M_w$ 50K:BASF Oppanol B PIB, $M_w$ 4 million) and 11 mg/mL CABOT CAB-O-SIL™ TS-530 fumed silica nanoparticles and gently inverting the vial and its contents repeatedly for 30 seconds. The coated devices were allowed to dry for at least two hours at room temperature and then were rinsed using a 30-second water wash. Residual water was removed using bottled air, and the conical devices or coupons were allowed to dry for at least one hour at room temperature before subsequent evaluation or experimentation.

The PIB/Tex-3 coated conical devices were placed into a standard 96-well culture plate (CELLTREAT® nontreated 96-well plate with lid, CELLTREAT®, Shirley, Mass.). Immediately before cell culture, the 96-well culture plate containing the tray of conical devices was sterilized for 5 minutes on each side (10 minutes in total) using UV radiation (CL-1000 Ultraviolet Crosslinker, available from UVP; wavelength range of 250-400 nm with a peak at 254 nm; 6.5 mM/cm$^2$). The 96-well culture plate containing the tray conical devices was then transferred to the cell culture hood after sterilization was complete.

The PIB/Tex-3 conical devices were evaluated for utility, non-cytotoxicity, and use in monitoring the growth of 3D eukaryotic cell aggregate(s) in drops containing eukaryotic cells suspended in culture medium as well as the use of the textured hydrophobic conical devices in a live/dead assay. HeLa cells were used in this experiment.

Figure 18:
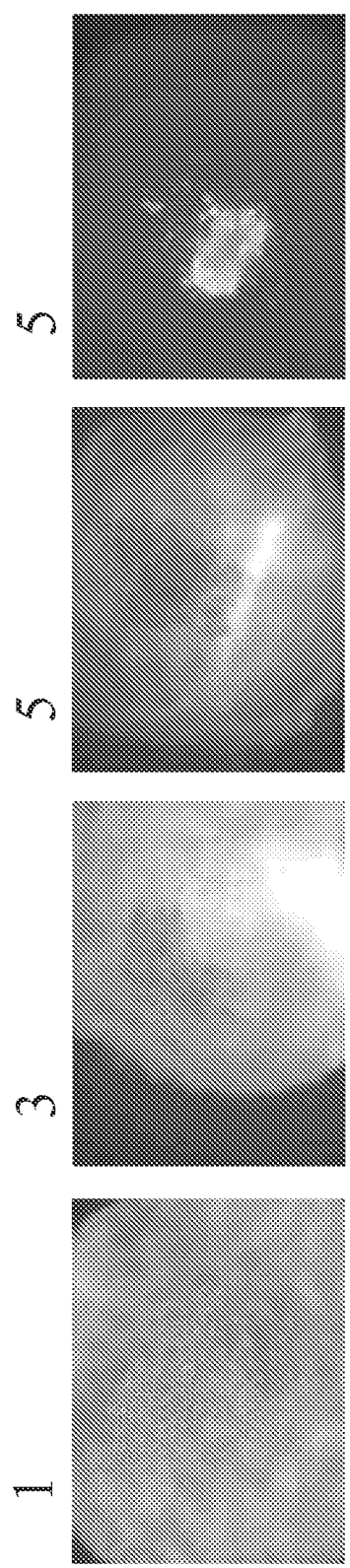
FIG. 18 are optical micrographs of HeLa cell aggregates (~1500 cells) in a PIB/Tex3-coated polystyrene conical device after 1, 3, and 5 days of cell culture in MEM with 10% FBS (the panel on the right shows the live/dead assay after five days of cell culture for the HeLa aggregate in the PIB/Tex3-coated polystyrene conical device)

HeLa cells growing in flasks were trypsinized and resuspended in growth medium (MEM containing 10% FBS). Thirty-five-µL aliquots of a HeLa cell suspension containing ~1500 cells were then added to the textured hydrophobic conical devices in the 96-well plate using a standard micropipette. A 250-µL aliquot of MEM containing 10% FBS was added to each of the outside wells of a 96-well plate (36 wells in total) to maintain a humid environment within the covered 96-well plate. The cell suspension in the devices/plate was incubated at 37° C., 5% $CO_2$ and monitored periodically for five days. Cell aggregation was observed after 1, 3, and 5 days of cell culture and a single aggregate from one of the PIB/Tex3-coated conical devices is shown in FIG. 18. Single 3D cell aggregate(s) in the PIB/Tex3-coated conical devices formed at Day 1, and decreased in diameter by Day 3 of culture. The cell aggregates remained positioned in or near the middle throughout the five-day experiment and did not attach or pin to the walls of the textured hydrophobic devices.

After five days of culture, cells were subjected to a live/dead cell assay within the PIB/Tex3-coated conical devices themselves. Because the serum in the MEM medium with 10% FBS quenches fluorescence, cell aggregate(s)/suspension were washed with sterile phosphate buffered saline solution (PBS) within the device itself in the following manner. A 5-µL aliquot of medium was removed from the top of the medium in each device without disturbing the aggregate(s). A 20-µL aliquot of sterile phosphate buffered saline solution (PBS) was then added to each device, and after 2-3 minutes, a 10-µL aliquot of medium/PBS was removed from the top of the medium in each device. A 2-µL aliquot of a 2-mM ethidium homodimer-1 (EthD-1) solution in 1:4 (v/v) DMSO:$H_2O$ and 1 µL of a 4-mM calcein AM solution in anhydrous DMSO was added to 997 µL of sterile PBS for a final concentration of ~4 µM EthD-1/~4 µM calcein AM for a live/dead viability/cytotoxicity assay (Live/Dead Viability/Cytotoxicity Kit, Cat#L3224, obtained from Invitrogen, Grand Island, N.Y.). EthD-1, which cannot permeate the membranes of viable cells, increases 40-fold in fluorescence upon binding to nucleic acids in cells with damaged cell membranes and produces a red fluorescence in dead cells ($\lambda_{em}$~495 nm/$\lambda_{em}$~635 nm). Calcein AM, which is able to permeate the cell membrane, produces a uniform green fluorescence in live cells ($\lambda_{ex}$~495 nm/$\lambda_{em}$~515 nm). A 30-µL aliquot of this ~4 µM EthD-1/~4 µM calcein AM stock solution was added to each of the devices containing aggregate(s). The solutions in the 96-well plate were incubated for 0.5 hours at 37° C., 5% $CO_2$ and then analyzed using the Leica DM IL LED inverted microscope with a Leica DFC 400 12V/200 mA digitizer and the Leica Application Suite.

The right panel in FIG. 18 shows the results of the live/dead assay for a single PIB/Tex3-coated device. Briefly, the right panel of FIG. 18 shows that at least 90% of the cells were live (green) cells whereas 10% of the cells or less were stained positive for EthD-1 (red) cells. Therefore, the live/dead assay indicates that the textured hydrophobic coatings are not toxic to the cells and the live/dead assay can successfully be performed within the textured hydrophobic conical devices. Thus, in some implementations, inventive devices can advantageously eliminate a step of removing the cell aggregates from the device before performing a live/dead assay.

This example demonstrates the textured hydrophobic coated devices do not interfere with microscopic observations and imaging requirements as well as demonstrates the noncytotoxicity of the coated surface, demonstrating the utility of the textured hydrophobic coated devices as cell culture vessels that can be used for both 3D cell culture and in the subsequent analysis of cell aggregates.

Example 7

White, high-impact polystyrene sheets (HIPS) with a thickness of 0.5 mm (0.020 inches) were purchased from Crown Plastics. Inc. (Plymouth, Minn.). These sheets were thermoformed using vacuum molding for the production of conical devices similar to FIG. 9 by either Hultman Design (Lindstrom, Minn.) or PN Products (Scandia, Minn.). A metal punch and hammer was then used to remove material at the apex of each conical device to form a smooth circular viewing aperture for each device. The diameter of the viewing apertures in the apex of the conical devices is in the range of about 1.0 mm to 1.2 mm.

The conical devices were cleaned prior to coating using the following protocol: (1) rinsing with two sequential 30-second washes of isopropanol and n-hexane, respectively; and (2) blowing dry using bottled air, then further drying for at least two hours at lab ambient conditions. The tray of conjoined conical devices, "PIB/Tex3-coated," was then coated by placing the tray in a 250-mL amber vial containing a dispersion in n-hexane of 10 mg/mL PIB (90:10 mixture of Aldrich PIB $M_w$ 50K:BASF Oppanol B PIB, $M_w$ 4 million) and 11 mg/mL CABOT CAB-O-SIL™ TS-530 fumed silica nanoparticles and gently inverting the vial and its contents repeatedly for 30 seconds. The coated devices were allowed to dry for at least two hours at room temperature and then were rinsed using a 30-second water wash. Residual water was removed using bottled air, and the conical devices or coupons were allowed to dry for at least one hour at room temperature before subsequent evaluation or experimentation.

The PIB/Tex-3 coated conical devices were placed into a standard 96-well culture plate (CELLTREAT® nontreated 96-well plate with lid, CELLTREAT®, Shirley, Mass.). Immediately before cell culture, the 96-well cell culture plate containing the tray of conical devices was sterilized for 5 minutes on each side (10 minutes in total) using UV radiation (CL-1000 Ultraviolet Crosslinker, available from UVP; wavelength range of 250-400 nm with a peak at 254 nm; 6.5 mM/cm$^2$). The 96-well culture plate containing the tray conical devices was then transferred to the cell culture hood after sterilization was complete.

Figure 19:
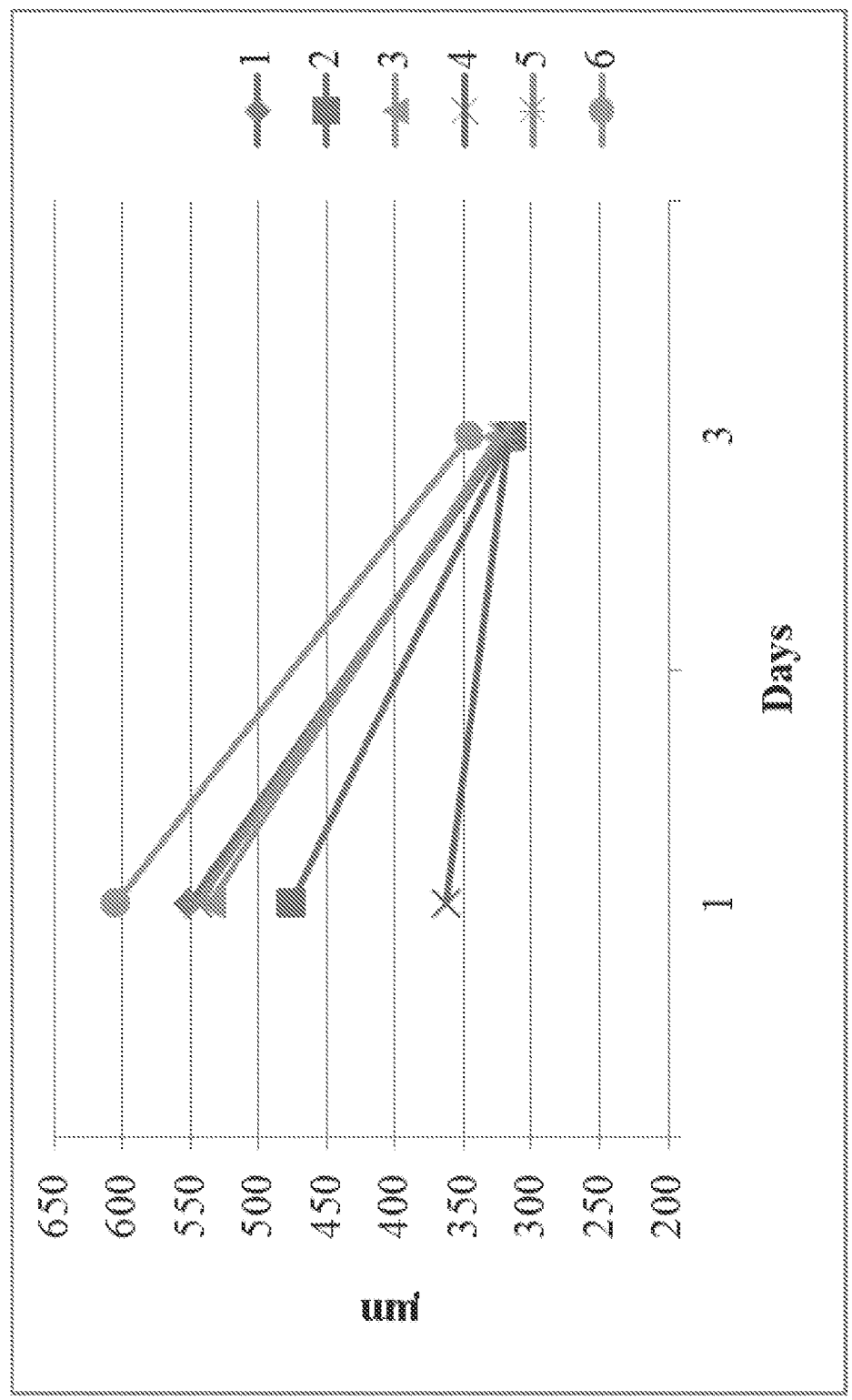
FIG. 19 is a graph of average aggregate diameter size (X-axis, in m) over 3 days (Y-axis) of 3D HeLa cell culture in PIB/Tex-3 coated conical devices.

The PIB/Tex-3 conical devices were evaluated for the production of cell aggregates of uniform size from 3D eukaryotic cell culture. HeLa cells were used in this experiment at the same cell seeding density (~1500 cells/device) and using the procedure described in EXAMPLE 6. The average aggregate diameter size (n=2) of six HeLa aggregates was measured after 1 and 3 days of culture for each aggregate and plotted in FIG. 19. As shown in both FIGS. 18 and 19, HeLa cell aggregates tighten (decrease in diameter) by Day 3 of culture.

HeLa aggregates on Day 1 of 3D cell culture were large with cells loosely attached to one another; their average diameters ranged from 363 µm to 605 µm (242 µm range). The average diameters of aggregates decreased both in size and in range over time: aggregate diameters were 315 µm to 346 µm on Day 3 (31 µm range). This example demonstrates the formation of uniform sized aggregates in PIB/Tex-3 coated devices when a constant cell seeding concentration is used.

What is claimed is:

1. A cell culture vessel comprising: a conical device having an inner surface being a hydrophobic surface; a frustum defining an open viewing aperture at a narrow end of the conical device, the open viewing aperture having a diameter in a range of 0.7 mm to 1.9 mm; and a suspension of cells in cell culture medium retained within the conical device at a location above the open viewing aperture.

2. The cell culture vessel according to claim 1, wherein the hydrophobic surface exhibits a contact angle of at least 120 degrees, or at least 130 degrees, or at least 140 degrees.

3. The cell culture vessel according to claim 1, wherein the hydrophobic surface comprises nanoparticles.

4. The cell culture vessel according to claim 3, wherein the hydrophobic surface comprises at least about 50% wt nanoparticles.

5. The cell culture vessel according to claim 1, wherein the conical device is opaque.

6. The cell culture vessel according to claim 1, wherein the conical device comprises a complex conical structure having a first taper angle and a second taper angle being at least 5 degrees greater than the first taper angle.

7. A cell culture vessel array comprising a plurality of cell culture vessels according to claim 1 conjoined to form an array of conical devices.

8. A cell culture assembly comprising:
a cell culture container comprising at least one chamber; and
a cell culture vessel according to claim 1 in registration with the chamber.

9. The cell culture assembly according to claim 8, wherein the cell culture container is light transparent and the cell culture vessel is opaque.

10. The cell culture vessel of claim 1 wherein the cell suspension comprises eukaryotic cells in serum.

11. The cell culture vessel of claim 1 wherein the cell suspension comprises a volume of 30 µL to 200 µL.

12. The cell culture vessel of claim 1 wherein the hydrophobic surface comprises a textured hydrophobic surface.

13. A kit comprising:
a cell culture vessel according to claim 1; and
a cell culture container comprising one or more chambers for cell culture.

14. The kit according to claim 13 wherein the cell culture vessel comprises a cell culture vessel array comprising a plurality of cell culture vessels conjoined to form an array of conical devices.

15. The kit according to claim 13 wherein the cell culture container comprises a cell culture plate.

16. A method for forming cell aggregates comprising steps of: (a) placing an amount of cell suspension into a cell culture vessel comprising a conical device having an inner surface being a hydrophobic surface, and a frustum defining an open viewing aperture at a narrow end of the conical device, the one viewing aperture having a diameter in a range of 0.7 mm to 1.9 mm wherein the cell suspension comprises cells in medium either with or without serum: and (b) allowing the formation of 3D cell aggregate(s) to occur within the cell suspension, wherein steps (a) and (b) are performed within the conical device at a location above the open viewing aperture.

17. The method according to claim 16 further comprising a step of periodically observing over time the growth of 3D cell aggregate(s) in each cell suspension by employing a microscope for viewing up through the viewing aperture of the conical device.

18. The method according to claim 16 wherein step (a) comprises placing 30 µL to 200 µL cell suspension into the cell culture vessel.

19. The method according to claim 16 wherein the cell culture vessel comprises a cell culture assembly that includes a cell culture container and one or more cell culture vessels.

20. The method according to claim 16, wherein the hydrophobic surface comprises nanoparticles.

* * * * *

UNITED STATES PATENT AND TRADEMARK OFFICE
CERTIFICATE OF CORRECTION

PATENT NO. : 10,072,241 B2
APPLICATION NO. : 14/774996
DATED : September 11, 2018
INVENTOR(S) : Laurie Lawin et al.

Page 1 of 1

It is certified that error appears in the above-identified patent and that said Letters Patent is hereby corrected as shown below:

On the Title Page

Column 1, Line 15 "(S) of EUKARYOTIC CELLS," filed Mar. 13, 2014, the" should read
-- (S) of EUKARYOTIC CELLS," filed Mar. 13, 2013, the --.

In the Claims

Column 28, Lines 35-37, Claim 16 "device, the one viewing aperture having a diameter in a range of 0.7 mm to 1.9 mm wherein the cell suspension comprises cells in medium either with or without serum: and" should read -- device, the open viewing aperture having a diameter in a range of 0.7 mm to 1.9 mm wherein the cell suspension comprises cells in medium either with or without serum; and --.

Signed and Sealed this
Ninth Day of October, 2018

Andrei Iancu
*Director of the United States Patent and Trademark Office*